United States Patent
Sun et al.

(10) Patent No.: US 11,034,663 B2
(45) Date of Patent: Jun. 15, 2021

(54) TETRAHYDRONAPHTHO[1,2-B]FURAN-2(3H)-ONE DERIVATIVES AND PREPARATION AND USES THEREOF

(71) Applicant: SHANGHAI QINGDONG BIOTECHNOLOGY CO., LTD., Shanghai (CN)

(72) Inventors: Qingyan Sun, Shanghai (CN); Weidong Zhang, Shanghai (CN)

(73) Assignee: SHANGHAI QINGDONG BIOTECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 16/741,844

(22) Filed: Mar. 13, 2020

(65) Prior Publication Data

US 2020/0199089 A1 Jun. 25, 2020

Related U.S. Application Data

(63) Continuation of application No. PCT/CN2018/095359, filed on Jul. 12, 2018.

(30) Foreign Application Priority Data

Jul. 14, 2017 (CN) .......................... 201710576021.1

(51) Int. Cl.
| | | |
|---|---|---|
| *C07D 307/83* | (2006.01) | |
| *C07D 413/06* | (2006.01) | |
| *C07D 405/06* | (2006.01) | |
| *A61P 19/02* | (2006.01) | |

(52) U.S. Cl.
CPC ............ *C07D 307/83* (2013.01); *A61P 19/02* (2018.01); *C07D 405/06* (2013.01); *C07D 413/06* (2013.01)

(58) Field of Classification Search
CPC .. C07D 307/83; C07D 405/06; C07D 413/06; A61P 19/02

USPC ........................................................ 514/232.8
See application file for complete search history.

(56) References Cited

FOREIGN PATENT DOCUMENTS

KR 20120020518 A 3/2012

OTHER PUBLICATIONS

Chen et al., Discovery of Potent Small-Molecule Inhibitors of Ubiquitin-Conjugating Enzyme UbcH5c from alpha-Santonin Derivatives, 2017, J. Med. Chem., 60, 6828-6852 (Year: 2017).*

* cited by examiner

*Primary Examiner* — Kristin A Vajda

(57) ABSTRACT

Disclosed are a tetrahydronaphtho[1,2-b]furan-2(3H)-one derivative of formula (I) and a method of making the same, where definitions of R, $R_1$ and $R_2$ herein are the same as those in the specification. It has been demonstrated by animal experiments that the tetrahydronaphtho[1,2-b]furan-2(3H)-one derivative can significantly inhibit the adjuvant-induced in Wistar male rats so that it can alleviate the primary and secondary lesions, showing a preventive activity to some extent. Therefore, the tetrahydronaphtho[1,2-b]furan-2(3H)-one derivative provided herein is applicable to the preparation of a drug for preventing/treating rheumatoid arthritis, and has promising clinical applications.

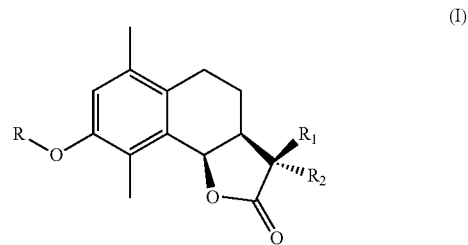

(I)

20 Claims, 2 Drawing Sheets

TETRAHYDRONAPHTHO[1,2-B]FURAN-2(3H)-ONE DERIVATIVES AND PREPARATION AND USES THEREOF

CROSS-REFERENCE TO RELATED APPLICATIONS

This application is a continuation of International Patent Application No. PCT/CN2018/095359, filed on Jul. 12, 2018, which claims the benefit of priority from Chinese Patent Application No. 201710576021.1, filed on Jul. 14, 2017. The contents of the aforementioned applications, including any intervening amendments thereto, are incorporated herein by reference.

TECHNICAL FIELD

The present application relates to pharmaceuticals, particularly to drugs and preparation thereof, and more particularly to tetrahydronaphtho[1,2-b]furan-2(3H)-one derivatives, their preparation and uses in the preparation of a drug for preventing and/or treating rheumatoid arthritis.

BACKGROUND OF THE INVENTION

Rheumatoid arthritis (RA), pertaining to autoimmune inflammatory diseases, is a chronic systemic inflammatory disease whose etiology remains unknown and has clinical manifestations mainly of chronic, symmetrical, polysynovial arthritis and extra-articular lesion. This disease frequently occurs in small joints, such as hand, wrist and foot joints, and is prone to recurrent attacks. Moreover, the RA generally shows symmetrical distribution. At the early stage, this disease is often characterized by redness, swelling, pain and dysfunction at the joints, and when it comes to the advanced stage, the joints may suffer from different levels of stiffness and deformity accompanied by atrophy of bones and skeletal muscles, which may easily cause disability. From the perspective of pathological change, the RA is a type of extensive inflammatory diseases which mainly involves synovial membranes (subsequently affecting articular cartilages, bone tissues, joint ligaments and tendons) and secondly involves some connective tissues such as serosa, heart, lung and eye. In addition to the joint lesions, the systemic manifestations of rheumatoid arthritis further include fever, fatigue, pericarditis, subcutaneous nodules, pleurisy, arteritis and peripheral neuropathy. However, there is still lack of effective therapies for RA, and the current treatment is mainly directed against the inflammation and sequelae. At present, the drugs for clinically treating RA primarily include non-steroidal anti-inflammatory drugs and adrenal cortical hormones. However, these drugs generally involve serious side effects, such as liver and kidney injury and pulmonary fibrosis, which render them unsuitable for the long-term treatment. Therefore, it is of great significance to develop a safe and effective drug for treating rheumatoid arthritis.

SUMMARY OF THE INVENTION

An object of this application is to provide a safe and effective drug for treating rheumatoid arthritis to overcome the defects in the prior art.

In a first aspect, this application provides a tetrahydronaphtho[1,2-b]furan-2(3H)-one derivative of formula (I):

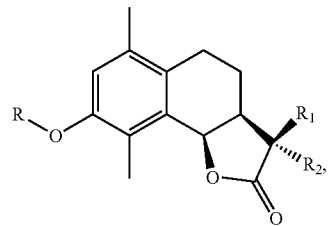

wherein:

R is selected from the group consisting of hydrogen, alkyl, cycloalkyl, hydroxy-substituted alkyl, alkenyl, alkynyl, aryl, alkylaryl, arylalkyl, arylalkenyl, arylalkynyl, heterocyclic group, trifluoromethyl, polyfluorosubstituted alkyl, cyano, cyanomethyl, acyl, carbamoyl, sulfonyl, sulfonamido and aryloxyalkyl;

$R_1$ and $R_2$ together form a terminal double bond; or
$R_1$ is hydrogen or deuterium and $R_2$ is

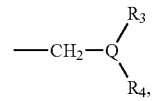

or a pharmaceutically-acceptable salt thereof formed by a reaction with an acid L or a quaternary ammonium salt thereof formed by a reaction with $R_5Z$, wherein Z is selected from the group consisting of fluorine, chlorine, bromine, iodine, p-toluenesulfonate, methanesulfonate, benzenesulfonate and trifluoromethanesulfonate; $R_5$ is selected from the group consisting of hydrocarbyl, cycloalkyl, hydroxy-substituted alkyl, alkenyl, alkynyl, aryl, heterocyclic group, aryl-substituted alkyl, arylalkenyl, arylalkynyl, cyano-substituted methyl, alkoxy-substituted alkyl and aryloxy-substituted alkyl; Q is N, O or S;

wherein the acid L is an inorganic acid or an organic acid; wherein the inorganic acid is selected from the group consisting of hydrofluoric acid, hydrochloric acid, hydrobromic acid, hydroiodic acid, sulfuric acid, sulfurous acid, nitric acid, phosphoric acid, phosphorous acid, carbonic acid, boric acid, selenious acid and phosphomolybdic acid; the organic acid is selected from the group consisting of acetic acid, propionic acid, hexanoic acid, oxalic acid, trifluoroacetic acid, glycolic acid, lactic acid, pyruvic acid, malonic acid, succinic acid, maleic acid, fumaric acid, hydroxymaleic acid, malic acid, tartaric acid, citric acid, mandelic acid, cinnamic acid, amino acid, benzoic acid, salicylic acid, 4-aminosalicylic acid, isonicotinic acid, methanesulfonic acid, ethanesulfonic acid, 2-hydroxyethanesulfonic acid, 1,2-ethanedisulfonic acid, benzenesulfonic acid, p-toluenesulfonic acid, naphthalene-2-sulfonic acid and camphorsulfonic acid, wherein the amino acid is selected from glycine, glutamic acid, proline, arginine and lysine;

$R_3$ and $R_4$ are independently selected from the group consisting of hydrogen, alkyl, cycloalkyl, hydroxy-substituted alkyl, alkenyl, alkynyl, aryl, alkylaryl, arylalkyl, arylalkenyl, arylalkynyl, heterocyclic group, trifluoromethyl, polyfluorosubstituted alkyl, cyano, cyanomethyl, acyl, carbamoyl, sulfonyl, sulfonamido and aryloxyalkyl; wherein $R_3$ and $R_4$ are the same or different.

In an embodiment, $R_3$ and $R_4$ form a 3- to 9-membered cyclic structure with a nitrogen atom, wherein the cyclic structure further comprises one or more substituents selected from the group consisting of hydrogen, alkyl, cycloalkyl, alkenyl, alkynyl, aryl, alkylaryl, arylalkyl, arylalkenyl, arylalkynyl and heterocyclic group.

In an embodiment, the tetrahydronaphtho[1,2-b]furan-2(3H)-one derivative is selected from compounds shown in the following table.

| ID | Structural formula |
|----|-------------------|
| 1  |                   |
| 2  |                   |
| 3  |                   |
| 4  |                   |
| 5  |                   |
| 6  |                   |
| 7  |                   |
| 8  |                   |
| 9  |                   |
| 10 |                   |
| 11 |                   |
| 12 |                   |

5
-continued
| ID | Structural formula |
|---|---|
| 13 | 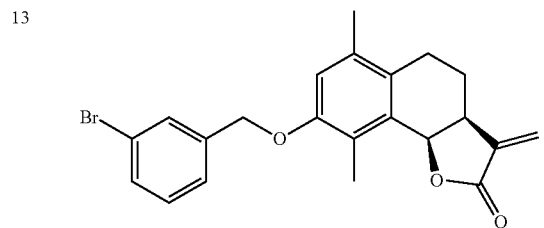 [SMILES: C=C1C(=O)O[C@H]2c3c(C)c(OCc4cccc(OC(F)F)c4)cc(C)c3CC[C@@H]12] |
| 14 | 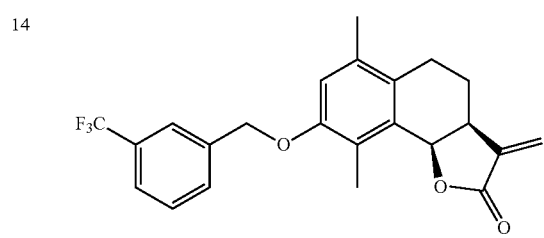 |
| 15 | 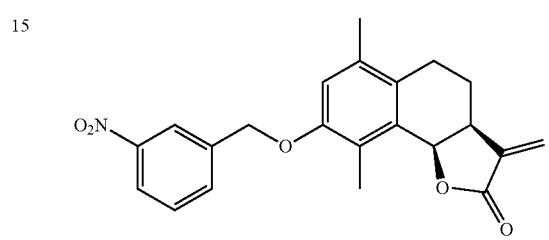 |
| 16 | 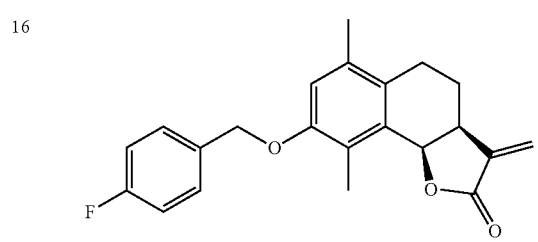 |
| 17 | 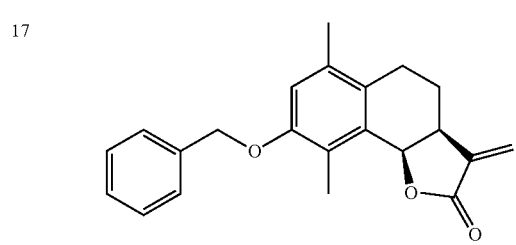 |
| 18 | 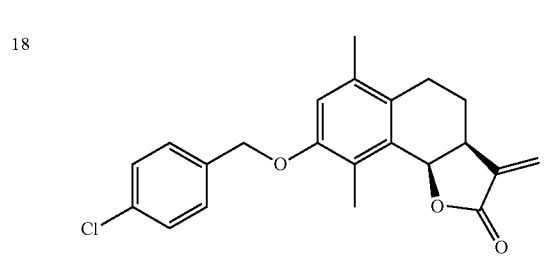 |
6
-continued
| ID | Structural formula |
|---|---|
| 19 | 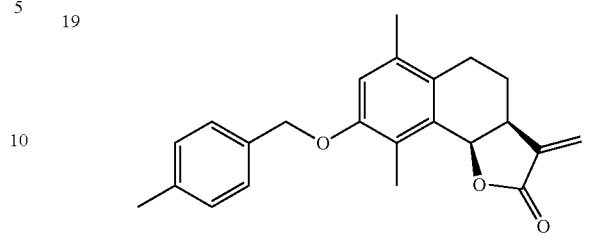 |
| 20 | 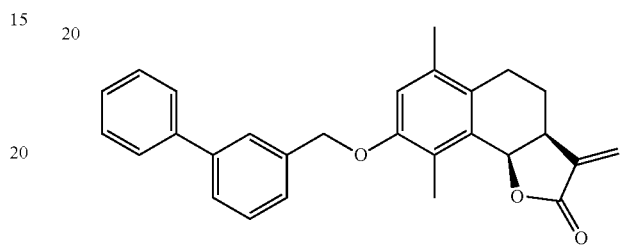 |
| 21 | 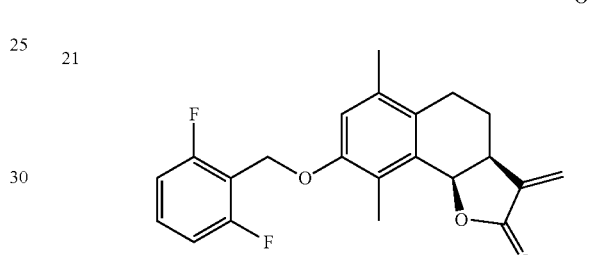 |
| 22 | 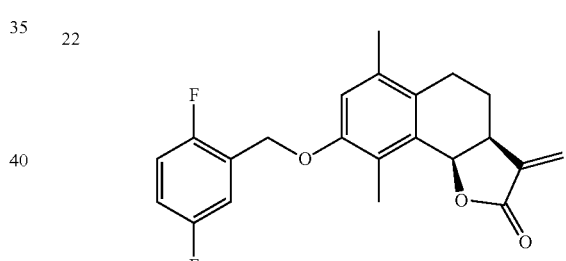 |
| 23 | 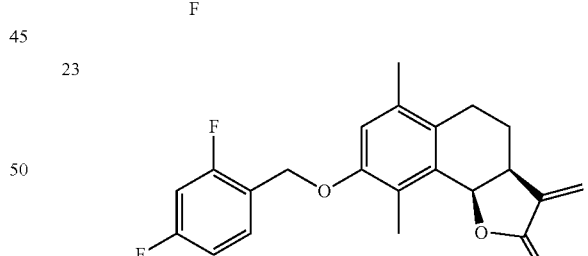 |
| 24 | 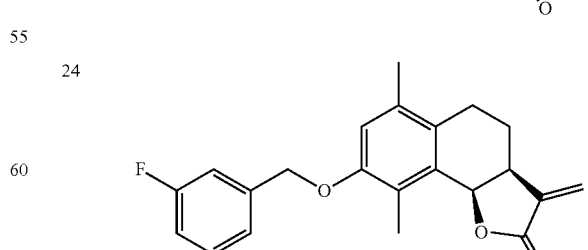 |

| ID | Structural formula |
|---|---|
| 25 | |
| 26 | |
| 27 | |
| 28 | |
| 29 | |
| 30 | |
| 31 | |
| 32 | |
| 33 | |
| 34 | |
| 35 | |
| 36 | |

-continued
| ID | Structural formula |
|---|---|
| 37 | 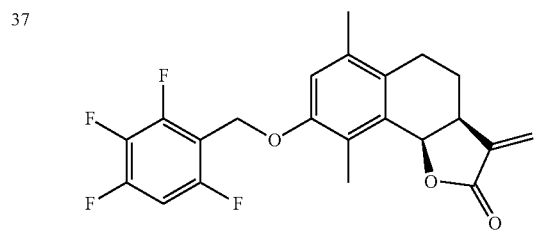 |
| 38 | 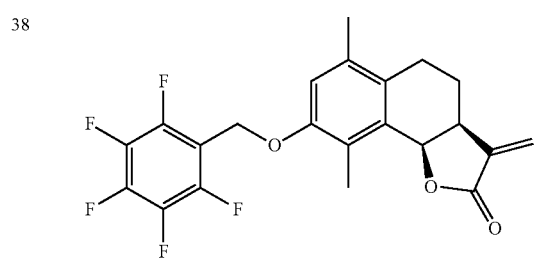 |
| 39 | 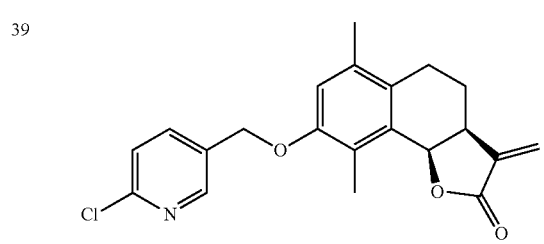 |
| 40 | 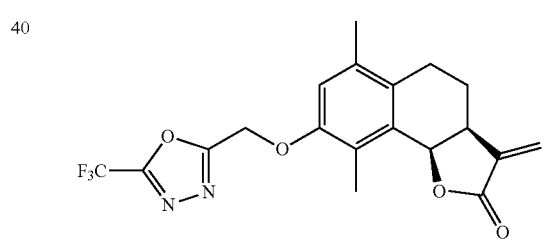 |
| 41 | 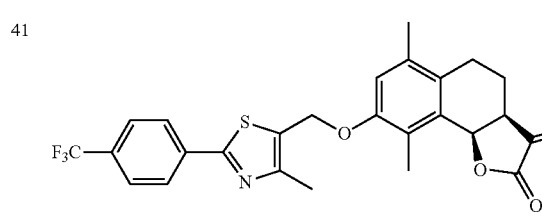 |
| 42 | 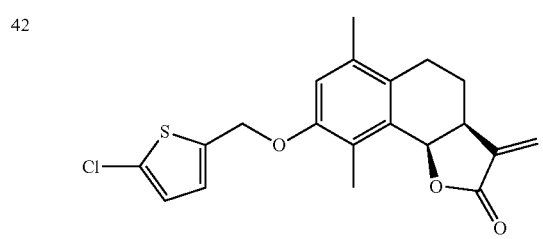 |
-continued
| ID | Structural formula |
|---|---|
| 43 | 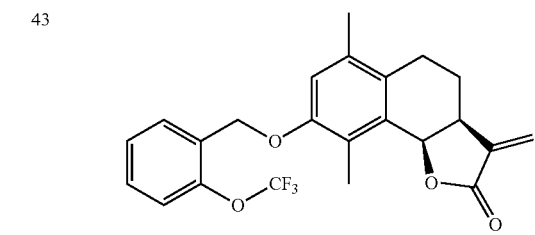 |
| 44 | 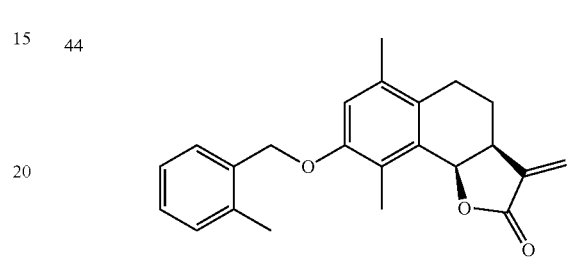 |
| 45 | 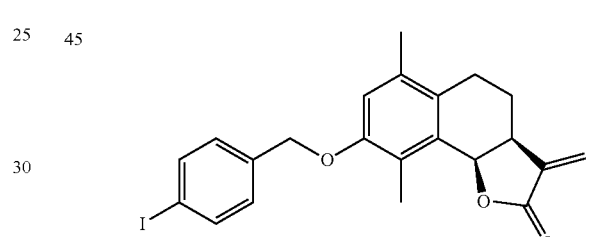 |
| 46 | 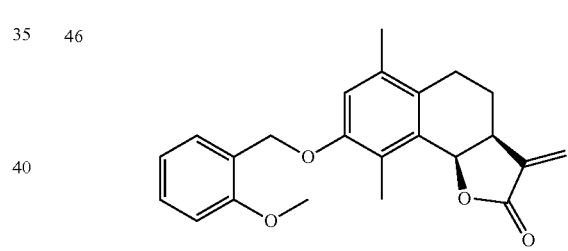 |
| 47 | 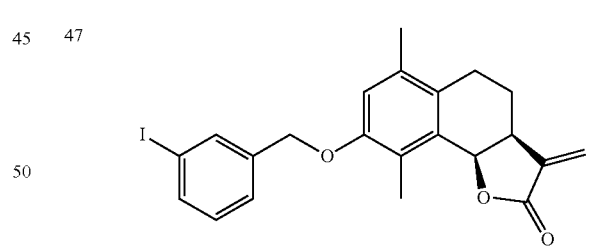 |
| 48 | 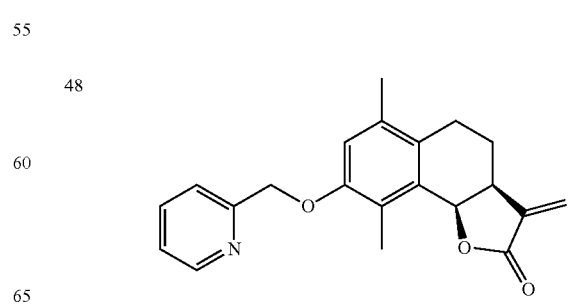 |

| ID | Structural formula |
|---|---|
| 49 | 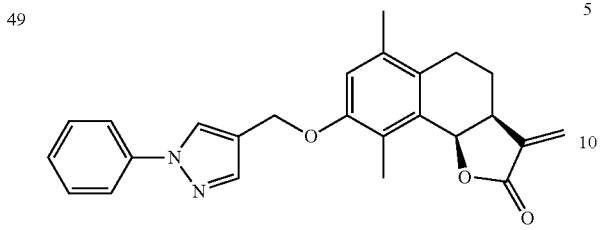 |
| 50 | 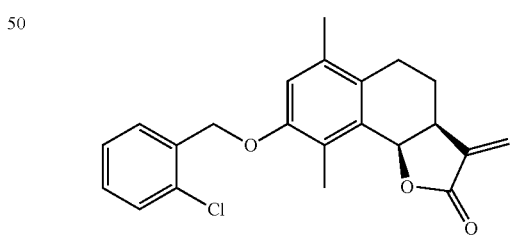 |
| 51 | 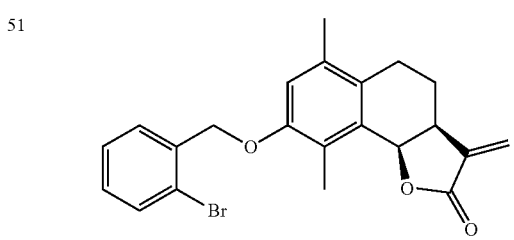 |
| 52 | 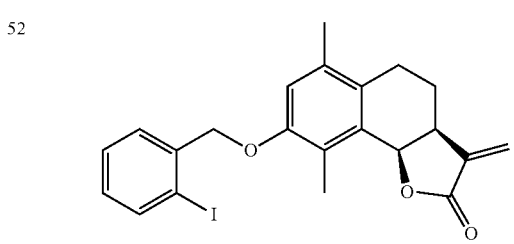 [SMILES: C=C1C(=O)O[C@H]2c3c(C)c(OCc4ccc(OC(F)(F)F)cc4)cc(C)c3CC[C@@H]12] |
| 53 | 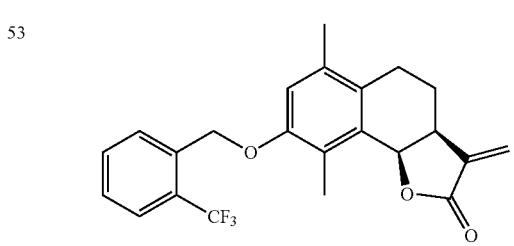 |
| 54, | 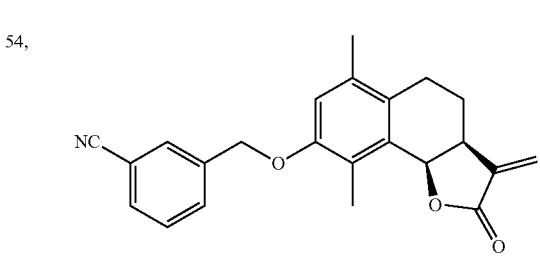 |
| ID | Structural formula |
|---|---|
| 55 | 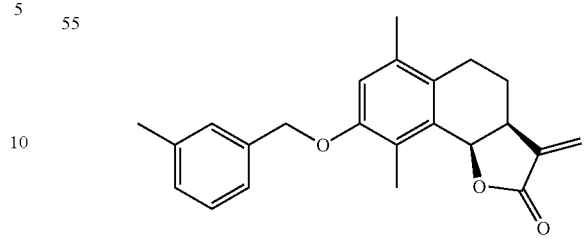 |
| 56 | 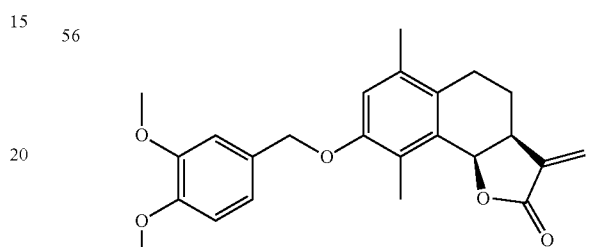 |
| 57 | 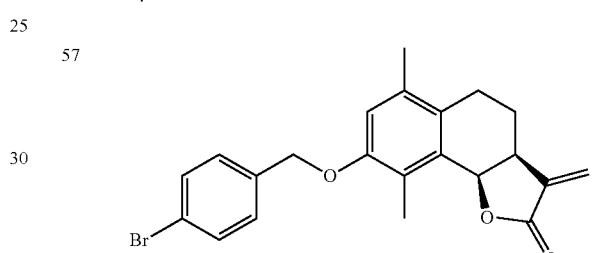 |
| 58 | 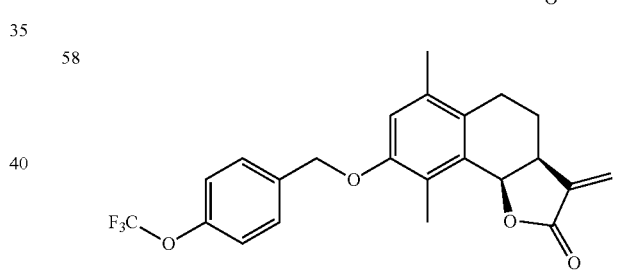 |
| 59 | 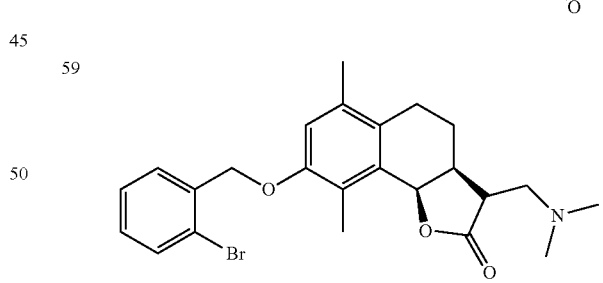 |
| 60 | 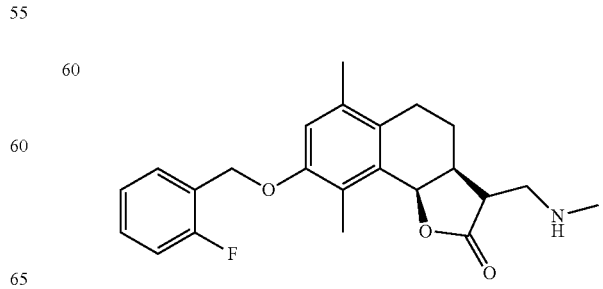 |

| ID | Structural formula |
|---|---|
| 61 | 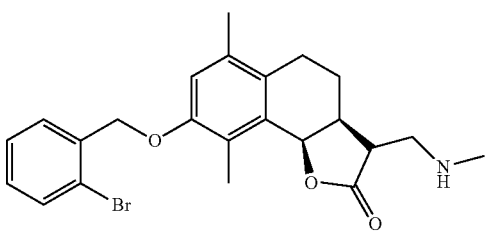 |
| 62 | 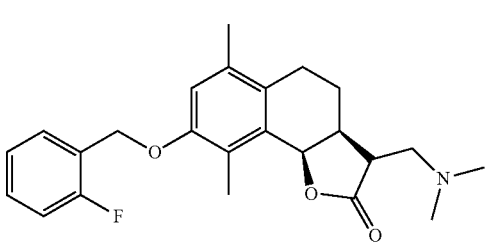 |
| 63 | 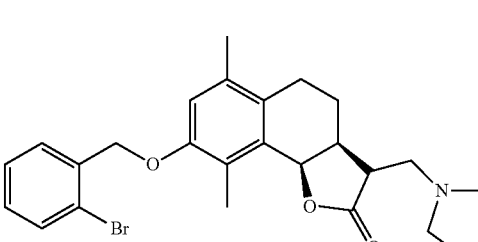 |
| 64 | 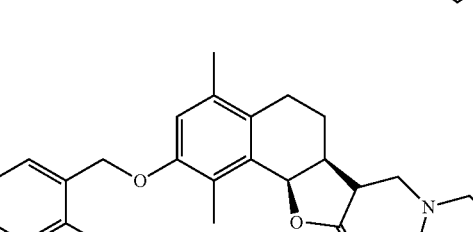 |
| 65 | 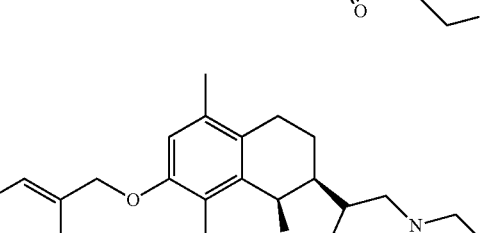 |
| 66 | 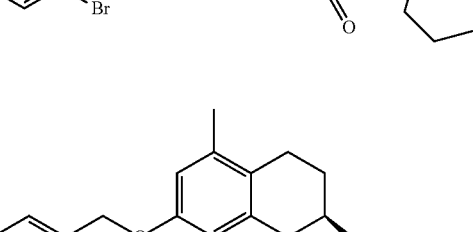 |
| ID | Structural formula |
|---|---|
| 67 | 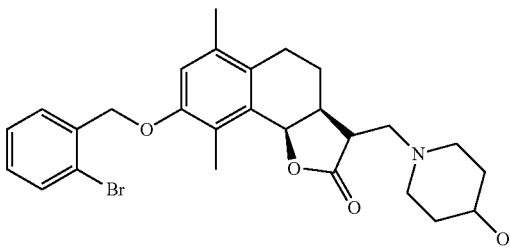 |
| 68 | 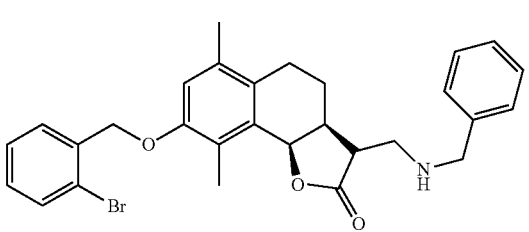 |
| 69 | 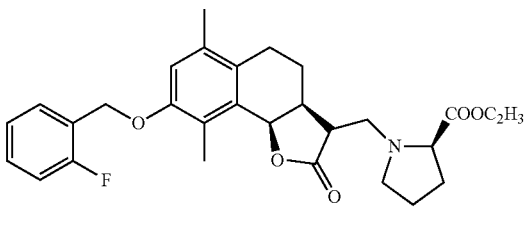 |
| 70 | 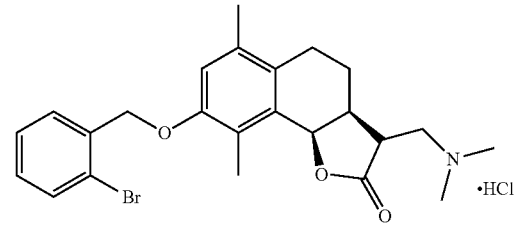 |
| 71 | 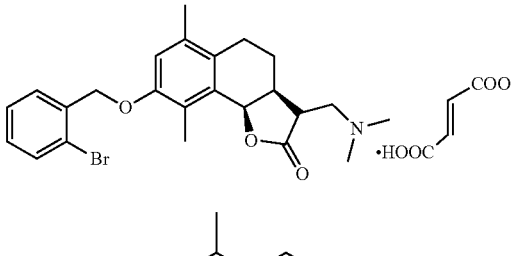 |
| 72 | 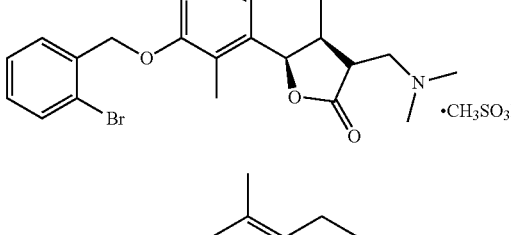 |
| 73 | 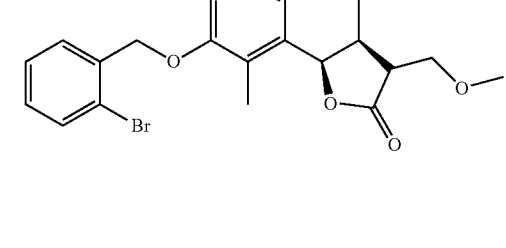 |

| ID | Structural formula |
| --- | --- |
| 74 | |
| 75 | |

Notes:
respective compounds in Tables 1-3 and Examples share the same ID.

In a second aspect, the invention further provides a method of preparing the tetrahydronaphtho[1,2-b]furan-2(3H)-one derivative, comprising:

(1) subjecting (3aS,5aS,9bS)-5a,9-dimethyl-3-methylene-3a,5,5a,9b-tetrahydronaphtho[1,2-b]furan-2,8(3H,4H)-dione (compound II) to rearrangement reaction in a solvent under an acidic condition in the presence of a catalyst to form (3aS,9bR)-6,9-dimethyl-3-methylene-2-oxo-2,3,3a,4,5,9b-hexahydronaphtho[1,2-b]furan-8-yl acetate (compound 1);

hydrolyzing a phenolic ester bond of the compound 1 in a solvent under a basic condition in the presence of a catalyst to produce (3aS,9bR)-8-hydroxy-6,9-dimethyl-3-methylene-3a,4,5,9b-tetrahydronaphtho[1,2-b]furan-2(3H)-one (compound 2);

(3) subjecting a free phenolic hydroxyl group of the compound 2 and a halogenated alkane to nucleophilic substitution in a solvent in the presence of a base and a catalyst to produce (3aS,9bR)-8-alkoxy-6,9-dimethyl-3-methylene-3a,4,5,9b-tetrahydronaphtho[1,2-b]furan-2(3H)-one (compound III), wherein the halogenated alkane is a halobenzyl or haloalkyl;

(4) subjecting an α-methylene lactone ring of the compound III and a nucleophile to Michael addition in a solvent in the presence of a base to form (3R or 3S,3aS,9bR)-8-substituted alkoxy-3-(substituted) aminomethyl/alkoxy/alkylthio-6,9-dimethyl-3a,4,5,9b-tetrahydronaphtho[1,2-b]furan-2(3H)-one (compound IV), wherein the nucleophile is an oxygen-containing alcohol or phenol, a nitrogen-containing aliphatic or aromatic amine or a sulfur-containing thiophenol or thiol; and (5) subjecting the compound IV and the acid L to salt-formation reaction in a solvent to produce a pharmaceutically acceptable salt (compound V) of (3R or 3S,3aS,9bR)-8-substituted alkoxy-3-disubstituted amino methyl-6,9-dimethyl-3a,4,5,9b-tetrahydronaphtho[1,2-b]furan-2(3H)-one, as shown in the following scheme:

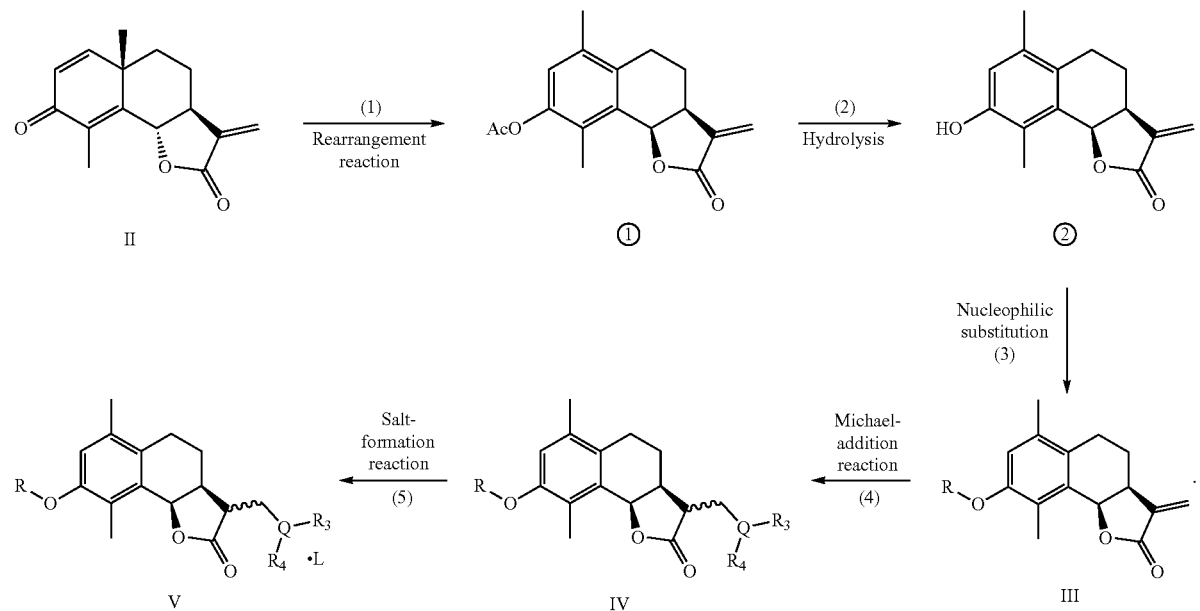

one (compound II) to rearrangement reaction in a solvent under an acidic condition in the presence of a catalyst to form (3aS,9bR)-6,9-dimethyl-3-methylene-2-oxo-2,3,3a,4,5,9b-hexahydronaphtho[1,2-b]furan-8-yl acetate (compound 1);

hydrolyzing a phenolic ester bond of the compound 1 in a solvent under a basic condition in the presence of a catalyst to produce (3aS,9bR)-8-hydroxy-6,9-dimethyl-3-methylene-3a,4,5,9b-tetrahydronaphtho[1,2-b]furan-2(3H)-one (compound 2);

The rearrangement reaction refers to the rearrangement of the starting material compound II to form compound 1 in the presence of the catalyst at a certain temperature in the solvent or under the solvent-free condition.

In an embodiment, $R_3$ and $R_4$ form a 3- to 9-membered cyclic structure with a nitrogen atom, wherein the cyclic structure further comprises one or more substituents selected from the group consisting of hydrogen, alkyl, cycloalkyl, alkenyl, alkynyl, aryl, alkylaryl, arylalkyl, arylalkenyl, arylalkynyl and heterocyclic group.

In an embodiment, in step (1), the solvent is selected from the group consisting of toluene, xylene, tetrahydrofuran, 2-methyltetrahydrofuran, dioxane, dichloromethane and dichloroethane; the catalyst is acetic anhydride or acetic acid/sulfuric acid; the rearrangement reaction is performed at −20° C.-25° C.; and a molar ratio of the catalyst to the compound II is 1:20-1:1.

In an embodiment, in step (1), the solvent is toluene or tetrahydrofuran; the rearrangement reaction is performed at −5° C.-15° C.; and the molar ratio of the catalyst to the compound II is 1:10-1:1.

In an embodiment, in step (1), the rearrangement reaction is performed at 0° C.-5° C.; and the molar ratio of the catalyst to the compound II is 1:3-1:1.

The hydrolysis in step (2) refers to the cleavage of the phenolic ester bond in compound 1 to form the compound 2 in the presence of the catalyst at a certain temperature in an appropriate solvent.

In an embodiment, in step (2), the solvent is selected from the group consisting of methanol, ethanol, isopropanol, toluene, tetrahydrofuran, 2-methyltetrahydrofuran, dioxane, dichloromethane, dichloroethane, acetone and butanone; the catalyst is selected from the group consisting of ammonia water, diethylamine, ethanolamine, formic acid and trifluoroacetic acid; the hydrolysis is performed at −20° C.-25° C.; and a molar ratio of the catalyst to the compound 1 is 30:1-1:1.

In an embodiment, in step (2), the solvent is methanol or tetrahydrofuran; the hydrolysis is performed at −5° C.-15° C.; and the molar ratio of the catalyst to the compound 1 is 20:1-1:1.

In an embodiment, in step (2), the hydrolysis is performed at 0° C.-5° C.; and the molar ratio of the catalyst to the compound 1 is 5:1-1:1.

The nucleophilic substitution in step (3) refers to a reaction in which the compound 2 is reacted in an appropriate solvent at a certain temperature in the presence of the base and the catalyst to form the compound (III).

In an embodiment, in step (3), the solvent is selected from methanol, ethanol, isopropanol, dimethyl sulfoxide, N,N-dimethylformamide, toluene, xylene, tetrahydrofuran, 2-methyltetrahydrofuran, ethyl acetate, dichloromethane, dichloroethane, chloroform, acetone and butanon; the base is an organic or inorganic base, wherein the organic base is selected from the group consisting of diethylamine, triethylamine, pyridine, piperidine, 4-dimethylaminopyridine, N,N-diisopropylethylamine, 1,8-diazabicycloundec-7-ene and 1,4-diazabicyclo[2.2.2]octane; the inorganic base is selected from the group consisting of sodium hydroxide, potassium hydroxide, potassium carbonate, sodium carbonate, cesium carbonate, potassium bicarbonate, sodium bicarbonate, sodium acetate, potassium acetate, sodium phosphate and potassium phosphate; the catalyst is selected from the group consisting of tetrabutylammonium chloride, tetrabutylammonium bromide, tetrabutylammonium iodide, tetrabutylammonium hydrogen sulfate, benzyltriethylammonium chloride and dodecyltriethylammonium chloride; the nucleophilic substitution is performed at −30° C.-60° C.; a molar ratio of the base to the compound 2 is 6:1-1:1; and a molar ratio of the catalyst to the compound 2 is 1:20-1:1.

In an embodiment, in step (3), the solvent is acetone, ethanol or tetrahydrofuran; the base is triethylamine, sodium acetate or potassium acetate; the catalyst is tetrabutylammonium iodide; the nucleophilic substitution is performed at −10° C.-35° C.; the molar ratio of the base to the compound 2 is 3:1-1:1; and the molar ratio of the catalyst to the compound 2 is 1:10-1:1.

In an embodiment, in step (3), the nucleophilic substitution is performed at 0° C.-25° C.; the molar ratio of the base to the compound 2 is 2:1-1:1; and the molar ratio of the catalyst to the compound 2 is 1:3-1:1.

The Michael-addition reaction in step (4) of the method refers to the addition of the methylene on the a-methylene lactone ring in the compound III to form the compound IV in an appropriate solvent at a certain temperature in the presence of an organic base.

In an embodiment, in step (4), the solvent is selected from methanol, ethanol, propanol, isopropanol, dimethyl sulfoxide, N,N-dimethylformamide, toluene, xylene, tetrahydrofuran, 2-methyltetrahydrofuran, ethyl acetate, dichloromethane, dichloroethane, chloroform, acetone and butanone; the base is an organic or inorganic base, wherein the organic base is selected from the group consisting of diethylamine, triethylamine, pyridine, piperidine, 4-dimethylaminopyridine, N,N-diisopropylethylamine, 1,8-diazabicycloundec-7-ene and 1,4-diazabicyclo[2.2.2]octane; the inorganic base is selected from the group consisting of sodium hydroxide, potassium hydroxide, potassium carbonate, sodium carbonate, cesium carbonate, potassium bicarbonate, sodium bicarbonate, sodium acetate, potassium acetate, sodium phosphate and potassium phosphate; the Michael addition is performed at −30° C.-60° C.; and a molar ratio of the base to the compound III is 8:1-1:1.

In an embodiment, in step (4), the solvent is methanol, ethanol or tetrahydrofuran; the base is triethylamine, sodium acetate or potassium acetate; the Michael addition is performed at −10° C.-35° C.; the molar ratio of the base to the compound III is 5:1-1:1.

In an embodiment, in step (4), the Michael addition is performed at 0° C.-25° C.; and the molar ratio of the second base to the compound III is 3:1-1:1.

The salt-formation reaction in step (5) of the method refers to a reaction in which the compound IV is reacted with a pharmaceutically-acceptable acid to form the target compound V in an appropriate solvent at a certain temperature.

In an embodiment, in step (5), the solvent is selected from methanol, ethanol, isopropanol, dimethyl sulfoxide, N,N-dimethylformamide, toluene, xylene, tetrahydrofuran, 2-methyltetrahydrofuran, ethyl acetate, dichloromethane, dichloroethane, chloroform, acetone and butanone; the salt-formation reaction is performed at 0° C.-60° C.; the acid is an inorganic acid or an organic acid, wherein the inorganic acid is selected from the group consisting of hydrochloric acid, hydrobromic acid, sulfuric acid, nitric acid and phosphoric acid; the organic acid is selected from the group consisting of acetic acid, propionic acid, hexanoic acid, oxalic acid, trifluoroacetic acid, glycolic acid, pyruvic acid, malonic acid, succinic acid, maleic acid, fumaric acid, hydroxymaleic acid, malic acid, tartaric acid, citric acid, mandelic acid, cinnamic acid, amino acid, benzoic acid, salicylic acid, 4-aminosalicylic acid, isonicotinic acid, methanesulfonic acid, ethanesulfonic acid, 2-hydroxyethanesulfonic acid, 1,2-ethanedisulfonic acid, benzenesulfonic acid, p-toluenesulfonic acid, naphthalene-2-sulfonic acid and camphorsulfonic acid, wherein the amino acid is selected from glycine, glutamic acid, arginine and lysine; and a molar ratio of the acid L to the compound IV is 3:1-1:8.

In an embodiment, in step (5), the solvent is ethanol or dichloromethane; the salt-formation reaction is performed at 5°C.-35° C.; and the molar ratio of the acid L to the compound IV is 1:1-1:5.

In an embodiment, in step (5), the salt-formation reaction is performed at 15° C.-25° C.; and the molar ratio of the acid L to the compound IV is 1:1-1:3.

In a third aspect, the invention further provides a method of treating rheumatoid arthritis in a patient in need thereof, comprising:

administering an effective amount of a pharmaceutical composition comprising the tetrahydronaphtho[1,2-b]furan-2(3H)-one derivative as an active ingredient to the patient.

In an embodiment, the pharmaceutical composition further comprises a pharmaceutically-acceptable adjuvant, and a dosage form of the pharmaceutical composition is tablet, dispersible tablet, buccal tablet, orally disintegrating tablet, sustained release tablet, capsule, soft capsule, dripping pill, granule, injection, powder injection, or aerosol.

It has been demonstrated by animal experiments that the tetrahydronaphtho[1,2-b]furan-2(3H)-one derivative of the invention can significantly inhibit the adjuvant-induced rheumatoid arthritis in Wistar male rats, so that it can alleviate the primary and secondary lesions, providing a preventive effect to some extent. Therefore, the tetrahydronaphtho[1,2-b]furan-2(3H)-one derivative of the invention is applicable to the preparation of a drug for preventing/treating rheumatoid arthritis. It has still not been reported about the application of the compound of formula (I) or a pharmaceutical composition thereof in the preparation of a drug for preventing/treating rheumatoid arthritis.

DETAILED DESCRIPTION OF EMBODIMENTS

Figure 1:
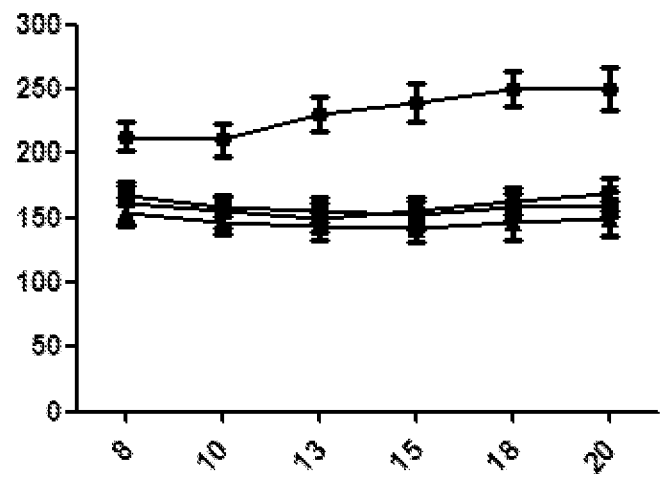
FIG. 1 shows the effect of daily therapeutic administration of compound 59 on weight of rats with adjuvant-induced arthritis, where the abscissa and ordinate respectively represent time (day) and weight (g).

The invention will be described in detail below with reference to the embodiments, but these embodiments are not intended to limit the invention.

Reagents and raw materials used herein are all commercially available or can be prepared according to the previously-published methods. Unless otherwise specified, the experiments mentioned below are performed under normal conditions or under conditions recommended by the manufacturer.

EXAMPLE 1

Preparation of (3aS,9bR)-6,9-dimethyl-3-methylene-2-oxo-2,3,3a,4,5,9b-hexahydronaphtho[1,2-b]furan-8-yl acetate (Compound 1)

To a 250 mL round-bottomed flask were added 4.0 g of compound 2 (16.4 mmol) and 30 mL of acetic anhydride. Under stirring at 0° C., the reaction mixture was dropwise added with 1 mL of concentrated sulfuric acid and reacted. After the reaction was completed, the reaction mixture was poured into 100 mL of ice water, and then the reaction mixture was extracted with dichloromethane three times each for 50 mL. The organic phases were collected, combined, washed respectively with saturated sodium bicarbonate (100 mL×3) and saturated brine (50 mL×3), dried with anhydrous $Na_2SO_4$ and concentrated using a rotary evaporator at 40° C. and a vacuum degree of 0.1 MPa to give a crude product. The crude product was purified by silica gel column chromatography to give 3.7 g of compound 1 with a yield of 78.9%, where a mixture of petroleum ether and ethyl acetate in a ratio of 3:1 was used as an eluent.

$^1$H NMR (500 MHz, Chloroform-d) δ 6.87 (s, 1H), 6.31 (d, J=2.0 Hz, 1H), 5.72 (d, J=1.8 Hz, 1H), 5.57 (d, J=6.7 Hz, 1H), 3.31 (dddd, J=8.7, 6.8, 4.8, 1.9 Hz, 1H), 2.75 (ddd, J=16.7, 6.0, 4.6 Hz, 1H), 2.54 (ddd, J=16.7, 9.6, 4.5 Hz, 1H), 2.33 (s, 3H), 2.23 (d, J=3.9 Hz, 6H), 1.99 (ddd, J=13.6, 10.9, 4.8 Hz, 1H), 1.83 (ddt, J=13.7, 9.5, 4.8 Hz, 1H).

$^{13}$C NMR (125 MHz, Chloroform-d) δ 170.2, 169.8, 147.6, 139.8, 134.9, 134.6, 131.1, 129.2, 124.2, 121.8, 74.9, 39.4, 29.9, 26.0, 21.0, 19.7, 12.2.

EXAMPLE 2

Preparation of (3aS,9bR)-8-hydroxy-6,9-dimethyl-3-methylene-3a,4,5,9b-tetrahydronaphtho[1,2-b]furan-2(3H)-one (Compound 2)

500 mg of compound 1 (1.75 mmol) was added to a 25 mL flask and dissolved with 25 mL of methanol. The reaction mixture was dropwise added with 25 mL of $NH_3.H_2O$ under stirring at 0° C. and reacted. After the reaction was completed, the reaction mixture was evaporated under vacuum to remove the organic solvent and extracted with dichloromethane three times each for 30 mL. The organic phases were collected, combined, washed with 30 mL of saturated brine, dried with anhydrous $Na_2SO_4$ and concentrated using a rotary evaporator at 40° C. and a vacuum degree of 0.1 MPa to give a crude product. The crude product was purified by silica gel column chromatography to give 315 mg of compound 2 with a yield of 73.7%, where a mixture of dichloromethane and methanol in a ratio of 20:1 was used as an eluent.

$^1$H NMR (500 MHz, Chloroform-d) δ 6.68 (s, 1H), 6.30 (d, J=2.0 Hz, 1H), 5.71 (d, J=1.8 Hz, 1H), 5.59 (d, J=6.7 Hz, 1H), 4.66 (s, 1H), 3.30 (dtt, J=8.6, 4.7, 1.9 Hz, 1H), 2.70 (ddd, J=16.4, 6.0, 4.5 Hz, 1H), 2.49 (ddd, J=16.4, 9.6, 4.5 Hz, 1H), 2.31 (s, 3H), 2.19 (s, 3H), 1.96 (ddd, J=13.5, 10.8, 4.7 Hz, 1H), 1.86-1.75 (m, 1H).

$^{13}$C NMR (125 MHz, Chloroform-d) δ 170.4 152.0, 140.1, 134.6, 130.8, 128.8, 122.5, 121.6, 117.9, 75.3, 39.6, 26.2, 23.8, 19.7, 11.4.

EXAMPLE 3

Preparation of (3aS,9bR)-8-(2-fluorobenzyloxy)-6,9-dimethyl-3-methylene-3a,4,5,9b-tetrahydro naphtho [1,2-b]furan-2(3H)-one (Compound 3)

30 mg of compound 2 (0.12 mmol), 0.027 mL of 2-fluorobenzyl chloride (0.25 mmol), 34 mg of $K_2CO_3$ (0.25 mmol) and 90 mg of TBAI (0.25 mmol) were added to a 50 mL flask and dissolved with 5 mL of acetone. The reaction mixture was reacted under stirring at room temperature. After the reaction was completed, the reaction mixture was filtered under vacuum, and the filtrate was evaporated under vacuum to remove the organic solvent and dried with anhydrous Na$_2$SO$_4$ to give a crude product. Then the crude product was purified by silica gel column chromatography to give 41 mg of the target compound (3aS,9bR)-8-(2-fluorobenzyloxy)-6,9-dimethyl-3-methylene-3a,4,5,9b-tetrahydronaphtho [1,2-b]furan-2(3H)-one with a yield of 96.3%, where a mixture of petroleum ether and ethyl acetate in a ratio of 5:1 was used as an eluent.

$^1$H NMR (500 MHz, Chloroform-d) δ 7.57-7.52 (m, 1H), 7.34-7.29 (m, 1H), 7.18 (t, J=7.5 Hz, 1H), 7.12-7.06 (m, 1H), 6.84 (s, 1H), 6.30 (d, J=2.0 Hz, 1H), 5.71 (d, J=1.8 Hz, 1H), 5.63 (t, J=6.6 Hz, 1H), 5.16-5.09 (m, 2H), 3.31 (ddd, J=9.6, 6.8, 4.9 Hz, 1H), 2.72 (ddd, J=16.4, 6.0, 4.5 Hz, 1H), 2.52 (ddd, J=16.4, 9.6, 4.5 Hz, 1H), 2.36 (s, 3H), 2.24 (s, 3H), 1.97 (ddd, J=13.5, 10.9, 4.7 Hz, 1H), 1.82 (dtd, J=13.9, 9.6, 4.4 Hz, 1H).

$^{13}$C NMR (125 MHz, Chloroform-d) δ 170.4, 154.9, 140.2, 134.2, 130.7, 129.5, 129.5, 129.0, 126.4, 124.4, 124.4, 121.5, 115.4, 115.2, 75.2, 64.5, 64.5, 39.6, 26.3, 23.8, 20.1, 11.7.

Compounds 4-58 in Table 1 were synthesized according to the process in Example 3.

Compound 4 was prepared with a yield of 65.0%.
$^1$H NMR (500 MHz, Chloroform-d) δ 7.55 (dd, J=8.1, 7.1 Hz, 1H), 7.22 (dd, J=9.3, 1.8 Hz, 1H), 7.12-7.08 (m, 1H), 6.73 (s, 1H), 6.31 (d, J=2.0 Hz, 1H), 5.71 (d, J=1.8 Hz, 1H), 5.62 (d, J=6.7 Hz, 1H), 5.01 (s, 2H), 3.32 (ddd, J=9.5, 6.9, 4.9 Hz, 1H), 2.71 (ddd, J=16.4, 6.2, 4.5 Hz, 1H), 2.52 (ddd, J=16.3, 9.4, 4.4 Hz, 1H), 2.36 (s, 3H), 2.22 (s, 3H), 1.97 (ddd, J=13.5, 11.0, 4.7 Hz, 1H), 1.82 (dtd, J=13.8, 9.5, 4.4 Hz, 1H).

$^{13}$C NMR (125 MHz, Chloroform-d) δ 170.3, 154.6, 140.1, 139.5, 139.5, 134.2, 133.7, 130.9, 129.2, 126.3, 123.7, 123.7, 121.6, 115.3, 115.0, 75.2, 69.3, 39.6, 26.3, 23.7, 20.1, 11.8.

Compound 5 was prepared with a yield of 60.6%.
$^1$H NMR (500 MHz, Chloroform-d) δ 7.66 (d, J=8.1 Hz, 2H), 7.56 (d, J=8.0 Hz, 2H), 6.77 (s, 1H), 6.31 (d, J=2.0 Hz, 1H), 5.72 (d, J=1.8 Hz, 1H), 5.63 (d, J=6.7 Hz, 1H), 5.12 (s, 2H), 3.32 (dtd, J=9.5, 4.9, 2.9 Hz, 1H), 2.72 (ddd, J=16.4, 6.2, 4.5 Hz, 1H), 2.52 (ddd, J=16.4, 9.4, 4.4 Hz, 1H), 2.38 (s, 3H), 2.23 (s, 3H), 2.01-1.94 (m, 1H), 1.83 (dtd, J=13.8, 9.5, 4.4 Hz, 1H).

$^{13}$C NMR (125 MHz, Chloroform-d) δ 170.3, 154.7, 141.7, 140.1, 134.2, 130.9, 129.1, 127.2 (4C), 126.3, 125.7, 125.7 121.6, 115.0, 75.2, 69.8, 39.6, 26.3, 23.8, 20.1, 11.8.

Compound 6 was prepared with a yield of 99.7%.
$^1$H NMR (500 MHz, Chloroform-d) δ 6.94 (d, J=15.0 Hz, 2H), 6.83 (s, 1H), 6.31 (d, J=2.0 Hz, 1H), 5.72 (d, J=1.3 Hz, 1H), 5.61 (dd, J=14.2, 6.7 Hz, 1H), 5.04-4.92 (m, 2H), 3.35-3.27 (m, 1H), 2.78-2.66 (m, 1H), 2.54 (ddq, J=19.0, 9.5, 4.4 Hz, 1H), 2.39-2.24 (m, 15H), 1.97 (ddd, J=9.0, 4.5, 1.6 Hz, 1H), 1.85-1.82 (m, 1H).

$^{13}$C NMR (125 MHz, Chloroform-d) δ 170.5, 155.6, 152.1, 140.2, 138.2 (2C), 134.1, 130.6, 130.4, 129.1(2C), 129.0, 128.5, 126.4, 121.5, 117.9, 114.8, 75.3, 65.3, 39.6, 29.8, 26.4, 23.8, 19.6, 11.6.

Compound 7 was prepared with a yield of 87.0%.
$^1$H NMR (500 MHz, Chloroform-d) δ 7.30 (t, J=7.9 Hz, 1H), 7.02 (d, 1=7.2 Hz, 2H), 6.89-6.84 (m, 1H), 6.80 (s, 1H), 6.30 (d, J=2.0 Hz, 1H), 5.71 (d, J=1.7 Hz, 1H), 5.63 (d, J=6.7 Hz, 1H), 5.04 (s, 2H), 3.31 (ddd, J=9.5, 6.8, 4.9 Hz, 1H), 2.71 (dt, J=16.4, 5.3 Hz, 1H), 2.56-2.47 (m, 1H), 2.37 (s, 3H), 2.23 (s, 3H), 1.96 (ddd, J=13.5, 10.9, 4.7 Hz, 1H), 1.82 (dtd, J=13.8, 9.6, 4.4 Hz, 1H).

$^{13}$C NMR (125 MHz, Chloroform-d) δ 170.4, 159.9, 155.1, 140.2, 139.2, 134.1, 130.7, 129.7, 128.7, 126.3, 121.5, 119.4, 115.2, 113.4, 112.8, 75.3, 70.5, 55.4, 39.6, 26.3, 23.8, 20.1, 11.8.

Compound 8 was prepared with a yield of 39.3%.
$^1$H NMR (500 MHz, Chloroform-d) δ 8.08-8.04 (m, 1H), 7.92-7.88 (m, 1H), 7.86 (d, J=8.3 Hz, 1H), 7.62 (d, J=6.9 Hz, 1H), 7.56-7.51 (m, 2H), 7.51-7.46 (m, 1H), 6.96 (s, 1H), 6.31 (d, J=1.6 Hz, 1H), 5.71 (s, 1H), 5.63 (d, J=6.6 Hz, 1H), 5.48 (s, 2H), 3.31 (dd, J=4.7, 2.6 Hz, 1H), 2.74 (dt, J=16.4, 5.2 Hz, 1H), 2.54 (ddd, J=16.1, 9.4, 4.4 Hz, 1H), 2.31 (s, 3H), 2.27 (s, 3H), 1.98 (dq, J=15.5, 4.9 Hz, 1H), 1.84 (dtd, J=13.8, 9.6, 4.4 Hz, 1H).

$^{13}$C NMR (125 MHz, Chloroform-d) δ 170.4, 155.2, 140.2, 134.2, 133.9, 132.9, 131.6, 130.8, 129.0, 128.8, 126.5, 126.5, 126.3, 126.0, 125.5, 123.8, 121.5, 115.1, 75.3, 69.3, 39.6, 29.8, 26.4, 23.8, 20.2, 11.7.

Compound 9 was prepared with a yield of 85.3%.
$^1$H NMR (500 MHz, Chloroform-d) δ 7.40 (d, J=8.0 Hz, 2H), 7.28 (dd, J=7.5, 0.9 Hz, 1H), 7.00 (s, 1H), 6.33 (d, J=2.0 Hz, 1H), 5.74 (d, J=1.7 Hz, 1H), 5.63 (d, J=6.7 Hz, 1H), 5.27 (s, 2H), 3.33 (ddd, J=9.5, 6.8, 4.9 Hz, 1H), 2.79-2.73 (m, 1H), 2.56 (ddd, J=16.3, 9.5, 4.5 Hz, 1H), 2.32 (s, 3H), 2.31 (s, 3H), 2.00 (ddd, J=13.4, 10.8, 4.8 Hz, 1H), 1.85 (dtd, J=13.9, 9.6, 4.4 Hz, 1H).

$^{13}$C NMR (125 MHz, Chloroform-d) δ 170.4, 155.1, 140.2, 137.1, 134.2, 132.6, 130.7, 130.4, 129.3, 128.6 (3C), 127.0, 121.4, 116.0, 75.3, 66.3, 39.6, 26.3, 23.8, 20.1, 11.6.

Compound 10 was prepared with a yield of 85.5%.
$^1$H NMR (500 MHz, Chloroform-d) δ 7.77-7.62 (m, 3H), 7.44 (t, J=7.6 Hz, 1H), 6.84 (s, 1H), 6.31 (d, J=2.0 Hz, 1H), 5.72 (d, J=1.8 Hz, 1H), 5.63 (d, J=6.7 Hz, 1H), 5.25 (d, J=5.0 Hz, 2H), 3.32 (ddd, J=9.6, 6.9, 4.9 Hz, 1H), 2.72 (dt, J=16.3, 5.2 Hz, 1H), 2.57-2.47 (m, 1H), 2.38 (s, 3H), 2.25 (s, 3H), 1.97 (ddd, J=13.5, 11.0, 4.7 Hz, 1H), 1.82 (dtd, J=13.9, 9.6, 4.4 Hz, 1H).

$^{13}$C NMR (125 MHz, Chloroform-d) δ 170.4, 154.4, 141.2, 140.1, 134.4, 133.3, 132.9, 130.9, 129.4, 128.4, 128.3, 126.3, 121.6, 117.2, 115.1, 111.0, 75.2, 68.1, 39.6, 26.3, 23.8, 20.1, 11.8.

Compound 11 was prepared with a yield of 89.3%.
$^1$H NMR (500 MHz, Chloroform-d) δ 7.35 (td, J=7.9, 5.9 Hz, 1H), 7.21 (d, J=7.6 Hz, 1H), 7.16 (d, J=9.6 Hz, 1H), 7.01 (td, J=8.4, 2.2 Hz, 1H), 6.77 (s, 1H), 6.31 (d, J=2.0 Hz, 1H), 5.72 (d, J=1.8 Hz, 1H), 5.63 (d, J=6.7 Hz, 1H), 5.05 (s, 2H), 3.31 (dtd, J=9.6, 4.9, 2.9 Hz, 1H), 2.71 (ddd, J=16.4, 6.1, 4.5 Hz, 1H), 2.51 (ddd, J=16.3, 9.6, 4.5 Hz, 1H), 2.37 (s, 3H), 2.23 (s, 3H), 2.01-1.93 (m, 1H), 1.82 (dtd, J=13.9, 9.6, 4.4 Hz, 1H).

$^{13}$C NMR (125 MHz, Chloroform-d) δ 170.4, 164.1, 154.8, 140.2, 140.1, 134.2, 130.8, 130.3, 130.2, 129.0, 126.3, 122.6, 121.6, 115.0, 114.1, 75.2, 69.8, 39.6, 26.3, 23.8, 20.2, 11.8.

Compound 12 was prepared with a yield of 96.8%.
$^1$H NMR (500 MHz, Chloroform-d) δ 7.45-7.42 (m, 1H), 7.34-7.28 (m, 3H), 6.76 (s, 1H), 6.31 (d, J=2.0 Hz, 1H), 5.71 (d, J=1.8 Hz, 1H), 5.63 (d, J=6.7 Hz, 1H), 5.03 (s, 2H), 3.31 (dtd, J=9.5, 4.9, 2.9 Hz, 1H), 2.71 (ddd, J=16.4, 6.2, 4.5 Hz, 1H), 2.52 (ddd, J=16.4, 9.5, 4.4 Hz, 1H), 2.37 (s, 3H), 2.23 (s, 3H), 1.96 (ddt, J=9.5, 6.1, 4.8 Hz, 1H), 1.82 (dtd, J=13.8, 9.5, 4.4 Hz, 1H).

$^{13}$C NMR (125 MHz, Chloroform-d) δ 170.4, 154.8, 140.1, 139.7, 134.6, 134.2, 130.9, 130.0, 129.0, 128.1, 127.3, 126.3, 125.2, 121.5, 115.2, 75.2, 69.9, 39.6, 26.3, 23.8, 20.1, 11.8.

Compound 13 was prepared with a yield of 99.8%.
$^1$H NMR (500 MHz, Chloroform-d) δ 7.59 (s, 1H), 7.46 (d, J=7.9 Hz, 1H), 7.37 (d, J=7.7 Hz, 1H), 7.27 (d, J=7.4 Hz, 1H), 6.76 (s, 1H), 6.31 (d, J=2.0 Hz, 1H), 5.71 (d, J=1.8 Hz, 1H), 5.63 (d, J=6.7 Hz, 1H), 5.02 (s, 2H), 3.32 (ddd, J=9.5, 6.9, 4.9 Hz, 1H), 2.72 (ddd, J=16.4, 6.1, 4.5 Hz, 1H), 2.52 (ddd, J=16.3, 9.4, 4.4 Hz, 1H), 2.37 (s, 3H), 2.23 (s, 3H), 1.97 (ddd, J=13.5, 11.0, 4.7 Hz, 1H), 1.82 (dtd, J=13.8, 9.5, 4.4 Hz, 1H).
$^{13}$C NMR (125 MHz, Chloroform-d) δ 170.4, 154.8, 140.1, 139.9, 134.2, 131.0, 130.9, 130.3, 130.2, 129.1, 126.3, 125.7, 122.8, 121.5, 115.2, 75.2, 69.8, 39.6, 26.3, 23.8, 20.1, 11.8.

Compound 14 was prepared with a yield of 84.5%.
$^1$H NMR (500 MHz, Chloroform-d) δ 7.70 (s, 1H), 7.65 (d, J=7.6 Hz, 1H), 7.59 (d, J=7.8 Hz, 1H), 7.52 (t, J=7.7 Hz, 1H), 6.79 (s, 1H), 6.31 (d, J=2.1 Hz, 1H), 5.71 (d, J=1.8 Hz, 1H), 5.63 (d, J=6.7 Hz, 1H), 5.10 (s, 2H), 3.32 (ddd, J=9.6, 6.9, 4.9 Hz, 1H), 2.72 (ddd, J=16.4, 6.2, 4.5 Hz, 1H), 2.52 (ddd, J=16.4, 9.5, 4.4 Hz, 1H), 2.37 (s, 3H), 2.23 (s, 3H), 2.02-1.93 (m, 1H), 1.83 (dtd, J=13.8, 9.5, 4.5 Hz, 1H).
$^{13}$C NMR (125 MHz, Chloroform-d) δ 170.4, 154.8, 140.1, 138.6, 134.3, 130.9, 130.5, 129.2 (2C), 129.2, 126.4, 125.3, 124.8, 124.0, 121.5, 115.2, 75.2, 70.0, 39.6, 26.3, 23.8, 20.1, 11.7.

Compound 15 was prepared with a yield of 70.7%.
$^1$H NMR (500 MHz, Chloroform-d) δ 8.31 (s, 1H), 8.19 (d, J=8.2 Hz, 1H), 7.80 (d, J=7.3 Hz, 1H), 7.58 (t, J=7.9 Hz, 1H), 6.77 (s, 1H), 6.31 (d, J=2.0 Hz, 1H), 5.72 (d, J=1.8 Hz, 1H), 5.64 (dd, J=6.4, 2.7 Hz, 1H), 5.15 (s, 2H), 3.32 (d, J=4.6 Hz, 1H), 2.71 (dd, J=15.5, 5.4 Hz, 1H), 2.57-2.52 (m, 1H), 2.37 (d, J=10.9 Hz, 3H), 2.23 (s, 3H), 1.98 (dd, J=13.6, 6.1 Hz, 1H), 1.88-1.80 (m, 1H).

Compound 16 was prepared with a yield of 92.8%.
$^1$H NMR (500 MHz, Chloroform-d) δ 7.45-7.37 (m, 2H), 7.10-7.06 (m, 2H), 6.79 (s, 1H), 6.31 (d, J=2.0 Hz, 1H), 5.71 (d, J=1.8 Hz, 1H), 5.62 (d, J=6.7 Hz, 1H), 5.01 (s, 2H), 3.31 (dtd, J=9.5, 4.9, 2.9 Hz, 1H), 2.72 (ddd, J=16.4, 6.2, 4.5 Hz, 1H), 2.55-2.48 (m, 1H), 2.35 (s, 3H), 2.23 (s, 3H), 1.96 (ddt, J=9.6, 6.2, 4.8 Hz, 1H), 1.82 (dtd, J=13.9, 9.6, 4.4 Hz, 1H).
$^{13}$C NMR (125 MHz, Chloroform-d) δ 170.4, 163.5, 155.0, 140.1, 134.1, 133.3, 130.8, 129.1, 129.1, 128.9, 126.3, 121.5, 115.7, 115.5, 115.3, 75.2, 70.1, 39.6, 26.3, 23.8, 20.1, 11.7.

Compound 17 was prepared with a yield of 85.0%.
$^1$H NMR (500 MHz, Chloroform-d) δ 7.46-7.43 (m, 2H), 7.39 (t, J=7.5 Hz, 2H), 7.33 (t, J=7.3 Hz, 1H), 6.81 (s, 1H), 6.31 (d, J=2.0 Hz, 1H), 5.71 (d, J=1.8 Hz, 1H), 5.63 (d, J=6.7 Hz, 1H), 5.06 (s, 2H), 3.31 (dtd, J=9.6, 4.9, 2.9 Hz, 1H), 2.72 (ddd, J=16.4, 6.1, 4.5 Hz, 1H), 2.52 (ddd, J=16.3, 9.5, 4.4 Hz, 1H), 2.37 (s, 3H), 2.23 (s, 3H), 2.00-1.93 (m, 1H), 1.82 (dtd, J=13.8, 9.6, 4.4 Hz, 1H).
$^{13}$C NMR (125 MHz, Chloroform-d) δ 170.4, 155.1, 140.2, 137.6, 134.1, 130.7, 128.7, 128.7 (2C), 127.9, 127.3 (2C), 126.3, 121.5, 115.2, 75.3, 70.7, 39.6, 26.4, 23.8, 20.1, 11.7.

Compound 18 was prepared with a yield of 99.2%.
$^1$H NMR (500 MHz, Chloroform-d) δ 7.37 (d, J=1.2 Hz, 4H), 6.76 (s, 1H), 6.31 (d, J=2.0 Hz, 1H), 5.71 (d, J=1.8 Hz, 1H), 5.62 (d, J=6.7 Hz, 1H), 5.02 (s, 2H), 3.31 (ddd, J=9.6, 6.9, 4.9 Hz, 1H), 2.71 (ddd, J=16.4, 6.1, 4.5 Hz, 1H), 2.51 (ddd, J=16.4, 9.4, 4.4 Hz, 1H), 2.35 (s, 3H), 2.22 (s, 3H), 2.00-1.93 (m, 1H), 1.82 (dtd, J=13.9, 9.5, 4.4 Hz, 1H).
$^{13}$C NMR (125 MHz, Chloroform-d) δ 170.4, 154.9, 140.1, 136.1, 134.2, 133.7, 130.8, 128.9, 128.9(2C), 128.6 (2C), 126.3, 121.5, 115.2, 75.2, 69.9, 39.6, 26.3, 23.8, 20.1, 11.7.

Compound 19 was prepared with a yield of 98.2%.
$^1$H NMR (500 MHz, Chloroform-d) δ 7.33 (d, J=8.0 Hz, 2H), 7.20 (d, J=7.8 Hz, 2H), 6.81 (s, 1H), 6.30 (d, J=2.0 Hz, 2H), 5.71 (d, J=1.8 Hz, 1H), 5.62 (d, J=6.7 Hz, 1H), 5.01 (s, 2H), 3.30 (dtd, J=9.6, 4.9, 2.9 Hz, 1H), 2.71 (ddd, J=16.3, 6.1, 4.5 Hz, 1H), 2.51 (ddd, J=16.3, 9.5, 4.4 Hz, 1H), 2.37 (s, 3H), 2.35 (s, 3H), 2.23 (s, 3H), 1.96 (ddt, J=9.5, 6.1, 4.8 Hz, 1H), 1.82 (dtd, J=13.9, 9.6, 4.4 Hz, 1H).
$^{13}$C NMR (125 MHz, Chloroform-d) δ 170.5, 155.2, 140.2, 137.7, 134.5, 134.1, 130.6, 129.3(2C), 128.6, 127.4 (2C), 126.3, 121.4, 115.3, 75.3, 70.7, 39.6, 26.4, 23.8, 21.3, 20.1, 11.7.

Compound 20 was prepared with a yield of 96.7%.
$^1$H NMR (500 MHz, Chloroform-d) δ 7.67 (s, 1H), 7.63-7.59 (m, 2H), 7.58-7.54 (m, 1H), 7.49-7.42 (m, 4H), 7.39-7.34 (m, 2H), 6.84 (s, 1H), 6.31 (d, J=2.0 Hz, 1H), 5.71 (d, J=1.8 Hz, 1H), 5.63 (d, J=6.7 Hz, 1H), 5.12 (s, 2H), 3.31 (ddd, J=9.6, 6.8, 4.9 Hz, 1H), 2.72 (ddd, J=16.3, 6.1, 4.5 Hz, 1H), 2.52 (ddd, J=16.3, 9.5, 4.5 Hz, 1H), 2.39 (s, 3H), 2.24 (s, 3H), 1.97 (ddd, J=13.5, 11.0, 4.7 Hz, 1H), 1.83 (dtd, J=13.8, 9.6, 4.4 Hz, 1H).
$^{13}$C NMR (125 MHz, Chloroform-d) δ 170.4, 155.1, 141.7, 141.1, 140.2, 138.1, 134.1, 130.8, 129.1, 129.0(2C), 128.8, 127.5, 127.3(2C), 126.8, 126.4, 126.2, 126.1, 121.5, 115.3, 75.3, 70.8, 39.6, 26.3, 23.8, 20.1, 11.8.

Compound 21 was prepared with a yield of 81.0%.
$^1$H NMR (500 MHz, Chloroform-d) δ 7.32 (tt, J=8.4, 6.5 Hz, 1H), 6.93 (h, J=4.0 Hz, 3H), 6.30 (d, J=2.0 Hz, 1H), 5.70 (d, J=1.8 Hz, 1H), 5.59 (d, J=6.7 Hz, 1H), 5.09 (s, 2H), 3.29 (dddt, J=8.6, 6.7, 4.8, 1.8 Hz, 1H), 2.72 (ddd, J=16.4, 6.1, 4.5 Hz, 1H), 2.56-2.48 (m, 1H), 2.26 (d, J=6.5 Hz, 6H), 2.01-1.90 (m, 1H), 1.81 (dtd, J=13.9, 9.6, 4.4 Hz, 1H).
$^{13}$C NMR (125 MHz, Chloroform-d) δ 170.4, 161.1, 161.1, 155.0, 140.2, 134.2, 130.7, 130.7, 130.6, 129.4, 127.0, 121.4, 116.1, 111.6, 111.4, 75.2, 59.2, 39.6, 26.3, 23.8, 20.1, 11.5.

Compound 22 was prepared with a yield of 93.5%.
$^1$H NMR (500 MHz, Chloroform-d) δ 7.28 (s, 1H), 7.07-6.96 (m, 2H), 6.80 (s, 1H), 6.31 (d, J=1.9 Hz, 1H), 5.71 (d, J=1.7 Hz, 1H), 5.63 (d, J=6.7 Hz, 1H), 5.09 (s, 2H), 3.35-3.28 (m, 1H), 2.72 (dt, J=16.4, 5.3 Hz, 1H), 2.56-2.48 (m, 1H), 2.37 (s, 3H), 2.24 (s, 3H), 2.01-1.93 (m, 1H), 1.82 (dtd, J=13.8, 9.5, 4.3 Hz, 1H).
$^{13}$C NMR (125 MHz, Chloroform-d) δ 170.4, 154.6, 140.1, 134.3, 130.9, 129.3, 126.3, 121.5, 116.4, 115.9, 115.8, 115.7, 115.7, 115.6, 115.1, 75.2, 63.9, 39.6, 26.3, 23.8, 20.1, 11.7.

Compound 23 was prepared with a yield of 83.3%.
$^1$H NMR (500 MHz, Chloroform-d) δ 7.53-7.46 (m, 1H), 6.95-6.88 (m, 1H), 6.85 (ddd, J=10.2, 8.9, 2.5 Hz, 1H), 6.82 (s, 1H), 6.31 (d, J=2.0 Hz, 1H), 5.71 (d, J=1.8 Hz, 1H), 5.62 (d, J=6.7 Hz, 1H), 5.10-5.02 (m, 2H), 3.31 (dtd, J=9.5, 4.9, 2.9 Hz, 1H), 2.72 (ddd, J=16.4, 6.1, 4.5 Hz, 1H), 2.52 (ddd, J=16.3, 9.5, 4.4 Hz, 1H), 2.34 (s, 3H), 2.24 (s, 3H), 2.00-1.93 (m, 1H), 1.82 (dtd, J=13.8, 9.6, 4.4 Hz, 1H).
$^{13}$C NMR (125 MHz, Chloroform-d) δ 170.4, 154.7, 140.1, 134.2, 130.8, 130.5, 129.2, 126.4, 121.5, 115.3, 111.5, 104.1, 103.9, 103.7, 75.2, 64.1, 64.1, 39.6, 26.3, 23.8, 20.1, 11.7.

Compound 24 was prepared with a yield of 85.2%.
$^1$H NMR (500 MHz, Chloroform-d) δ 6.97 (dd, J=7.9, 2.2 Hz, 2H), 6.78-6.71 (m, 2H), 6.31 (d, J=2.1 Hz, 1H), 5.71 (d, J=1.8 Hz, 1H), 5.63 (d, J=6.7 Hz, 1H), 5.03 (s, 2H), 3.32 (ddd, J=9.6, 6.9, 4.9 Hz, 1H), 2.72 (ddd, J=16.3, 6.2, 4.5 Hz, 1H), 2.52 (ddd, J=16.4, 9.4, 4.5 Hz, 1H), 2.38 (s, 3H), 2.23 (s, 3H), 1.97 (ddd, J=13.5, 11.0, 4.7 Hz, 1H), 1.83 (dtd, J=13.9, 9.6, 4.5 Hz, 1H).

¹³C NMR (125 MHz, Chloroform-d) δ 170.3, 164.4, 154.5, 140.1, 134.3, 131.0, 129.2, 126.3, 121.6, 115.0, 109.8, 109.6, 103.4, 103.2, 103.0, 75.1, 69.4, 39.6, 26.3, 23.8, 20.1, 11.8.

Compound 25 was prepared with a yield of 95.9%.

¹H NMR (500 MHz, Chloroform-d) δ 7.53 (d, J=8.3 Hz, 1H), 7.29 (dd, J=8.3, 2.1 Hz, 1H), 7.26-7.24 (m, 1H), 6.77 (s, 1H), 6.30 (d, J=2.0 Hz, 1H), 5.72 (d, J=1.8 Hz, 1H), 5.62 (d, J=6.7 Hz, 1H), 5.09 (s, 2H), 3.31 (dddt, J=8.7, 6.7, 4.7, 1.8 Hz, 1H), 2.71 (ddd, J=16.4, 6.1, 4.5 Hz, 1H), 2.51 (ddd, J=16.4, 9.5, 4.5 Hz, 1H), 2.37 (s, 3H), 2.23 (s, 3H), 1.96 (ddt, J=9.6, 6.1, 4.8 Hz, 1H), 1.81 (dtd, J=13.9, 9.6, 4.4 Hz, 1H).

¹³C NMR (125 MHz, Chloroform-d) δ 170.4, 154.5, 140.0, 137.0, 134.3, 133.9, 133.1, 130.8, 129.5, 129.2, 129.2, 127.4, 126.2, 121.6, 115.0, 75.2, 67.2, 39.5, 26.2, 23.7, 20.1, 11.7.

Compound 26 was prepared with a yield of 92.9%.

¹H NMR (500 MHz, Chloroform-d) δ 7.53 (d, J=1.9 Hz, 1H), 7.46 (d, J=8.2 Hz, 1H), 7.29-7.26 (m, 1H), 6.74 (s, 1H), 6.31 (d, J=2.0 Hz, 1H), 5.71 (d, J=1.8 Hz, 1H), 5.62 (d, J=6.7 Hz, 1H), 5.00 (s, 2H), 3.32 (ddd, J=9.5, 6.9, 4.9 Hz, 1H), 2.71 (ddd, J=16.4, 6.1, 4.5 Hz, 1H), 2.52 (ddd, J=16.4, 9.5, 4.5 Hz, 1H), 2.36 (s, 3H), 2.22 (s, 3H), 1.97 (ddd, J=13.5, 11.0, 4.7 Hz, 1H), 1.82 (dtd, J=13.8, 9.5, 4.4 Hz, 1H).

¹³C NMR (125 MHz, Chloroform-d) δ 170.4, 154.6, 140.0, 137.9, 134.3, 132.8, 131.9, 130.9, 130.7, 129.2, 129.1, 126.4, 126.3, 121.6, 115.1, 75.2, 69.3, 39.6, 26.3, 23.7, 20.1, 11.8.

Compound 27 was prepared with a yield of 90.7%.

¹H NMR (500 MHz, Chloroform-d) δ 7.92 (s, 2H), 7.85 (s, 1H), 6.78 (s, 1H), 6.32 (d, J=2.1 Hz, 1H), 5.72 (d, J=1.8 Hz, 1H), 5.63 (d, J=6.7 Hz, 1H), 5.15 (s, 2H), 3.33 (ddd, J=9.5, 7.0, 5.0 Hz, 1H), 2.73 (ddd, J=16.4, 6.3, 4.5 Hz, 1H), 2.58-2.49 (m, 1H), 2.38 (s, 3H), 2.24 (s, 3H), 1.98 (ddd, J=13.6, 11.1, 4.7 Hz, 1H), 1.84 (dtd, J=13.8, 9.5, 4.4 Hz, 1H).

¹³C NMR (125 MHz, Chloroform-d) δ 170.3, 154.5, 140.3, 140.0, 134.4, 132.2, 131.9, 131.2, 129.7, 127.2, 127.2, 126.4, 124.5, 122.3, 122.0, 121.6, 115.2, 75.1, 69.4, 39.5, 26.2, 23.8, 20.1, 11.7.

Compound 28 was prepared with a yield of 94.1%.

¹H NMR (500 MHz, Chloroform-d) δ 7.36 (d, J=8.7 Hz, 2H), 6.93 (d, J=8.7 Hz, 2H), 6.82 (s, 1H), 6.30 (d, J=2.0 Hz, 1H), 5.71 (d, J=1.8 Hz, 1H), 5.62 (d, J=6.7 Hz, 1H), 4.98 (s, 2H), 3.83 (s, 3H), 3.30 (dtd, J=9.6, 4.9, 3.0 Hz, 1H), 2.71 (ddd, J=16.4, 6.1, 4.5 Hz, 1H), 2.52 (ddd, J=16.3, 9.5, 4.4 Hz, 1H), 2.34 (s, 3H), 2.23 (s, 3H), 2.00-1.93 (m, 1H), 1.82 (dtd, J=13.9, 9.6, 4.4 Hz, 1H).

¹³C NMR (125 MHz, Chloroform-d) δ 170.4, 159.4, 155.2, 140.2, 134.0, 130.6, 129.6, 129.5, 129.0(2C), 128.6, 121.4, 115.4, 114.1(2C), 113.9, 75.3, 70.5, 39.6, 26.3, 23.7, 20.1, 11.7.

Compound 29 was prepared with a yield of 94.8%.

¹H NMR (500 MHz, Chloroform-d) δ 7.39 (t, J=7.9 Hz, 1H), 7.31-7.27 (m, 1H), 7.22 (s, 1H), 7.08 (dd, J=8.1, 1.9 Hz, 1H), 6.78 (s, 1H), 6.53 (t, J=73.9 Hz, 1H), 6.31 (d, J=2.0 Hz, 1H), 5.71 (d, J=1.8 Hz, 1H), 5.63 (d, J=6.7 Hz, 1H), 5.05 (s, 2H), 3.32 (dtd, J=9.6, 4.9, 2.9 Hz, 1H), 2.72 (ddd, J=16.4, 6.2, 4.5 Hz, 1H), 2.52 (ddd, J=16.3, 9.5, 4.4 Hz, 1H), 2.37 (s, 3H), 2.23 (s, 3H), 1.97 (ddt, J=13.5, 6.1, 4.7 Hz, 1H), 1.82 (dtd, J=13.8, 9.5, 4.4 Hz, 1H).

¹³C NMR (125 MHz, Chloroform-d) δ 170.4, 154.8, 151.6, 140.1, 139.9, 134.2, 130.9 130.1, 129.0, 126.3, 124.0, 121.5, 118.8, 118.3, 116.0, 115.2, 75.2, 70.0, 39.6, 26.3, 23.8, 20.1, 11.7.

Compound 30 was prepared with a yield of 95.2%.

¹H NMR (500 MHz, Chloroform-d) δ 7.29 (d, J=7.3 Hz, 1H), 7.14 (dt, J=14.9, 7.1 Hz, 2H), 6.86 (s, 1H), 6.30 (d, J=2.0 Hz, 1H), 5.71 (d, J=1.8 Hz, 1H), 5.62 (d, J=6.7 Hz, 1H), 5.02 (s, 2H), 3.31 (ddd, J=9.6, 6.8, 4.9 Hz, 1H), 2.73 (ddd, J=16.4, 6.1, 4.5 Hz, 1H), 2.53 (ddd, J=16.3, 9.5, 4.4 Hz, 1H), 2.38-2.12 (m, 12H), 1.97 (ddd, J=13.5, 10.9, 4.7 Hz, 1H), 1.83 (ddt, J=13.6, 9.5, 4.8 Hz, 1H).

¹³C NMR (125 MHz, Chloroform-d) δ 170.4, 155.2, 140.2, 137.2, 135.5, 135.2, 134.1, 130.7, 130.0, 128.6, 126.7, 126.3, 125.6, 121.4, 115.0, 75.3, 69.9, 39.6, 26.4, 23.8, 20.5, 20.2, 15.0, 11.7.

Compound 31 was prepared with a yield of 93.9%.

¹H NMR (500 MHz, Chloroform-d) δ 7.13-7.06 (m, 2H), 6.92 (dd, J=7.2, 2.5 Hz, 1H), 6.87 (s, 1H), 6.30 (d, J=2.0 Hz, 1H), 5.71 (d, J=1.8 Hz, 1H), 5.62 (d, J=6.7 Hz, 1H), 5.10 (s, 2H), 3.89 (d, J=5.5 Hz, 6H), 3.30 (ddd, J=9.6, 6.8, 4.9 Hz, 1H), 2.76-2.68 (m, 1H), 2.52 (ddd, J=16.3, 9.6, 4.4 Hz, 1H), 2.35 (s, 3H), 2.24 (s, 3H), 1.97 (ddd, J=13.5, 10.9, 4.7 Hz, 1H), 1.82 (dtd, J=13.9, 9.6, 4.4 Hz, 1H).

¹³C NMR (125 MHz, Chloroform-d) δ 170.4, 155.2, 152.7, 146.9, 140.2, 134.1, 131.5, 130.6, 128.6, 126.2, 124.3, 121.4, 120.9, 115.1, 112.2, 75.3, 65.7, 61.2, 55.9, 39.7 26.4, 23.8, 20.1, 11.8.

Compound 32 was prepared with a yield of 69.1%.

¹H NMR (500 MHz, Chloroform-d) δ 7.10-7.03 (m, 2H), 6.71 (s, 1H), 6.31 (d, J=2.0 Hz, 1H), 5.72 (d, J=1.8 Hz, 1H), 5.62 (d, J=6.7 Hz, 1H), 4.98 (s, 2H), 3.32 (dtd, J=9.5, 4.9, 2.8 Hz, 1H), 2.71 (ddd, J=16.4, 6.2, 4.5 Hz, 1H), 2.52 (ddd, J=16.4, 9.4, 4.5 Hz, 1H), 2.36 (s, 3H), 2.22 (s, 3H), 2.00-1.94 (m, 1H), 1.82 (dtd, J=13.8, 9.5, 4.4 Hz, 1H).

¹³C NMR (125 MHz, Chloroform-d) δ 170.3, 154.4, 140.0, 134.3, 131.0, 129.4, 126.3, 121.6(2C), 115.0(2C), 111.1, 111.0, 110.9, 110.9, 75.1, 69.0, 39.5, 26.2, 23.7, 20.1, 11.7.

Compound 33 was prepared with a yield of 82.9%.

¹H NMR (500 MHz, Chloroform-d) δ 6.92 (s, 1H), 6.50-6.46 (m, 2H), 6.29 (d, J=2.0 Hz, 1H), 5.70 (d, J=1.7 Hz, 1H), 5.58 (d, J=6.7 Hz, 1H), 5.01 (s, 2H), 3.80 (s, 3H), 3.29 (dtd, J=9.6, 4.9, 3.0 Hz, 1H), 2.71 (ddd, J=16.4, 6.0, 4.5 Hz, 1H), 2.51 (ddd, J=16.4, 9.5, 4.4 Hz, 1H), 2.26 (d, J=6.0 Hz, 6H), 1.96 (ddd, J=13.5, 10.9, 4.7 Hz, 1H), 1.81 (dtd, J=13.9, 9.6, 4.4 Hz, 1H).

¹³C NMR (125 MHz, Chloroform-d) δ 170.4, 163.8, 161.8, 161.7, 155.0, 140.2, 134.1 130.6, 129.3, 127.0, 121.4, 116.2, 105.4, 98.2, 97.9, 75.3 59.1, 55.9, 39.6, 26.3, 23.8, 20.0, 11.5.

Compound 34 was prepared with a yield of 68.4%.

¹H NMR (500 MHz, Chloroform-d) δ 7.93 (s, 1H), 7.56-7.51 (m, 2H), 6.82 (s, 1H), 6.31 (d, J=2.0 Hz, 1H), 5.72 (d, J=1.8 Hz, 1H), 5.64 (d, J=6.7 Hz, 1H), 5.14 (s, 2H), 3.33 (ddd, J=9.6, 6.9, 4.9 Hz, 1H), 2.73 (ddd, J=16.4, 6.2, 4.5 Hz, 1H), 2.53 (ddd, J=16.4, 9.4, 4.5 Hz, 1H), 2.39 (s, 3H), 2.25 (s, 3H), 1.98 (ddd, J=13.5, 11.0, 4.7 Hz, 1H), 1.83 (dtd, J=13.8, 9.5, 4.4 Hz, 1H).

¹³C NMR (125 MHz, Chloroform-d) δ 170.3, 154.6, 140.1, 136.5, 134.4, 131.0, 130.0(2C), 129.5, 126.4, 125.8, 125.8, 125.6, 125.6, 121.6, 115.3, 75.1, 67.6, 39.6, 26.3, 23.8, 20.1, 11.7.

Compound 35 was prepared with a yield of 91.5%.

¹H NMR (500 MHz, Chloroform-d) δ 7.45-7.40 (m, 1H), 7.14 (dd, J=8.9, 2.3 Hz, 1H), 6.87 (d, J=8.9 Hz, 1H), 6.82 (s, 1H), 6.31 (d, J=2.0 Hz, 1H), 5.71 (d, J=1.8 Hz, 1H), 5.64 (d, J=6.7 Hz, 1H), 5.05 (s, 2H), 3.88 (s, 3H), 3.32 (dtd, J=9.6, 4.9, 2.9 Hz, 1H), 2.72 (ddd, J=16.4, 6.1, 4.5 Hz, 1H), 2.52 (ddd, J=16.4, 9.5, 4.5 Hz, 1H), 2.38 (s, 3H), 2.24 (s, 3H), 2.01-1.93 (m, 1H), 1.83 (dtd, J=13.8, 9.6, 4.4 Hz, 1H).

$^{13}$C NMR (125 MHz, Chloroform-d) δ 170.4, 155.0, 155.0, 142.9, 140.2, 134.2, 130.7, 128.9(2C), 127.8, 126.4, 121.5, 121.2, 121.1, 115.3, 110.7, 75.2, 65.3, 55.9, 39.6, 26.3, 23.8, 20.1, 11.7.

Compound 36 was prepared with a yield of 82.7%.

$^1$H NMR (500 MHz, Chloroform-d) δ 7.47-7.38 (m, 4H), 7.12-7.03 (m, 4H), 6.79 (s, 1H), 6.28 (s, 1H), 5.71 (d, J=1.8 Hz, 1H), 5.62 (d, J=6.7 Hz, 1H), 5.01 (s, 2H), 3.31 (dtd, J=9.5, 4.9, 2.9 Hz, 1H), 2.72 (ddd, J=16.4, 6.2, 4.5 Hz, 1H), 2.55-2.48 (m, 1H), 2.35 (s, 3H), 2.23 (s, 3H), 1.96 (ddt, J=9.6, 6.2, 4.8 Hz, 1H), 1.82 (dtd, J=13.9, 9.6, 4.4 Hz, 1H).

$^{13}$C NMR (125 MHz, Chloroform-d) δ 170.6, 163.6, 155.2, 140.1, 134.1, 133.3, 130.8, 129.1, 129.1, 128.9, 126.3, 121.5, 115.7, 115.5, 115.3, 75.2, 70.1, 39.6, 26.3, 23.8, 20.1, 11.7.

Compound 37 was prepared with a yield of 74.1%.

$^1$H NMR (500 MHz, Chloroform-d) δ 6.90 (s, 1H), 6.83 (dtd, J=11.6, 5.8, 2.4 Hz, 1H), 6.30 (d, J=2.0 Hz, 1H), 5.71 (d, J=1.8 Hz, 1H), 5.59 (d, J=6.7 Hz, 1H), 5.05 (s, 2H), 3.30 (dddt, J=8.7, 6.7, 4.8, 1.8 Hz, 1H), 2.72 (ddd, J=16.4, 6.2, 4.5 Hz, 1H), 2.52 (ddd, J=16.4, 9.5, 4.5 Hz, 1H), 2.26 (s, 6H), 1.96 (ddt, J=9.5, 6.1, 4.8 Hz, 1H), 1.82 (dtd, J=13.8, 9.6, 4.4 Hz, 1H).

Compound 38 was prepared with a yield of 92.3%.

$^1$H NMR (500 MHz, Chloroform-d) δ 6.88 (s, 1H), 6.30 (d, J=2.0 Hz, 1H), 5.71 (d, J=1.8 Hz, 1H), 5.59 (d, J=6.7 Hz, 1H), 5.12-5.07 (m, 2H), 3.31 (ddd, J=9.5, 6.9, 4.9 Hz, 1H), 2.72 (ddd, J=16.4, 6.1, 4.5 Hz, 1H), 2.52 (ddd, J=16.5, 9.4, 4.4 Hz, 1H), 2.26 (s, 6H), 1.97 (ddt, J=13.5, 11.0, 4.7 Hz, 1H), 1.82 (dtd, J=13.8, 9.5, 4.4 Hz, 1H).

Compound 39 was prepared with a yield of 83.2%.

$^1$H NMR (500 MHz, Chloroform-d) δ 8.55 (s, 1H), 7.80 (dd, J=8.2, 2.2 Hz, 1H), 7.39 (d, J=8.2 Hz, 1H), 6.77 (s, 1H), 6.31 (d, J=2.0 Hz, 1H), 5.71 (d, J=1.7 Hz, 1H), 5.61 (d, J=6.7 Hz, 1H), 5.06 (s, 2H), 3.32 (ddd, J=9.4, 6.9, 4.9 Hz, 1H), 2.71 (dt, J=16.4, 5.3 Hz, 1H), 2.57-2.47 (m, 1H), 2.33 (s, 3H), 2.23 (s, 3H), 1.97 (ddd, J=13.4, 11.0, 4.7 Hz, 1H), 1.82 (dtd, J=13.8, 9.5, 4.4 Hz, 1H).

$^{13}$C NMR (125 MHz, Chloroform-d) δ 170.3, 154.4, 151.1, 148.7, 140.0, 138.4, 134.4, 132.4, 131.1, 129.5, 126.3, 124.7, 121.6, 115.1, 75.1, 67.4, 39.5, 26.2, 23.7, 20.1, 11.7.

Compound 40 was prepared with a yield of 81.6%.

$^1$H NMR (500 MHz, Chloroform-d) δ 6.85 (s, 1H), 6.31 (d, J=2.1 Hz, 1H), 5.72 (d, J=1.8 Hz, 1H), 5.60 (d, J=6.7 Hz, 1H), 5.32 (d, J=2.4 Hz, 2H), 3.32 (dddt, J=8.8, 6.8, 4.7, 1.9 Hz, 1H), 2.72 (ddd, J=16.5, 6.2, 4.5 Hz, 1H), 2.52 (ddd, J=16.5, 9.4, 4.5 Hz, 1H), 2.32 (s, 3H), 2.24 (s, 3H), 1.97 (ddt, J=13.6, 6.3, 4.7 Hz, 1H), 1.82 (dtd, J=13.8, 9.5, 4.4 Hz, 1H).

$^{13}$C NMR (125 MHz, Chloroform-d) δ 170.3, 164.9(2C), 153.7, 139.8, 134.7, 131.4 131.0, 126.9, 121.8(2C), 115.7, 75.0, 60.8, 39.4, 26.1, 23.8, 20.1, 11.6.

Compound 41 was prepared with a yield of 72.9%.

$^1$H NMR (500 MHz, Chloroform-d) δ 8.07-7.98 (m, 3H), 7.68 (dd, J=8.5, 2.2 Hz, 3H), 6.83 (s, 1H), 6.31 (d, J=2.0 Hz, 1H), 5.72 (d, J=1.8 Hz, 1H), 5.61 (d, J=6.7 Hz, 1H), 5.18 (d, J=1.2 Hz, 2H), 4.86 (s, 1H), 3.32 (ddd, J=9.6, 6.9, 4.9 Hz, 1H), 2.72 (dt, J=16.4, 5.3 Hz, 1H), 2.58-2.53 (m, 1H), 2.52 (s, 3H), 2.33 (s, 3H), 1.97 (ddd, J=13.5, 11.0, 4.7 Hz, 1H), 1.82 (dtd, J=13.9, 9.5, 4.5 Hz, 1H).

$^{13}$C NMR (125 MHz, Chloroform-d) δ 170.4, 164.8, 154.4, 151.6, 140.0, 136.8, 134.3, 132.5, 131.8, 131.5, 131.0, 129.6, 128.9, 126.7(2C), 126.1(2C), 121.7, 115.5, 75.2, 63.2, 57.1, 39.5, 26.2, 20.2, 15.6, 11.7.

Compound 42 was prepared with a yield of 74.4%.

$^1$H NMR (500 MHz, Chloroform-d) δ 6.77-6.69 (m, 1H), 6.68-6.62 (m, 1H), 6.58-6.47 (m, 1H), 6.30 (d, J=1.9 Hz, 1H), 5.72 (d, J=1.4 Hz, 1H), 5.59 (dd, J=15.0, 6.4 Hz, 1H), 4.17-4.13 (m, 1H), 4.11-4.01 (m, 1H), 3.29 (s, 1H), 2.75 (dt, J=16.3, 5.0 Hz, 1H), 2.54 (ddd, J=16.2, 9.6, 4.3 Hz, 1H), 2.37-2.26 (m, 3H), 2.25-2.15 (m, 3H), 2.00-1.93 (m, 1H), 1.79 (ddt, J=18.1, 9.8, 4.2 Hz, 1H).

$^{13}$C NMR (125 MHz, Chloroform-d) δ 170.4, 150.6, 142.0, 140.0, 133.3, 129.1, 127.5, 126.0, 125.7, 124.9, 124.3, 124.0, 121.6, 75.4, 39.5, 31.1, 29.8, 26.2, 24.7, 12.0.

Compound 43 was prepared with a yield of 95.2%.

$^1$H NMR (500 MHz, Chloroform-d) δ 7.64 (dd, J=7.3, 1.9 Hz, 1H), 7.34 (qd, J=7.5, 1.8 Hz, 2H), 7.31-7.27 (m, 1H), 6.79 (s, 1H), 6.31 (d, J=2.0 Hz, 1H), 5.71 (d, J=1.8 Hz, 1H), 5.63 (d, J=6.7 Hz, 1H), 5.13 (d, J=1.4 Hz, 2H), 3.31 (ddd, J=9.6, 6.8, 4.9 Hz, 1H), 2.72 (ddd, J=16.4, 6.0, 4.5 Hz, 1H), 2.52 (ddd, J=16.3, 9.5, 4.4 Hz, 1H), 2.37 (s, 3H), 2.23 (s, 3H), 1.97 (ddd, J=13.5, 10.9, 4.7 Hz, 1H), 1.82 (dtd, J=13.8, 9.6, 4.4 Hz, 1H).

$^{13}$C NMR (125 MHz, Chloroform-d) δ 170.4, 154.7, 146.7, 140.1, 134.3, 130.8, 130.4, 129.3, 129.1, 129.1, 127.2, 126.3, 121.5, 120.5, 120.5, 115.1, 75.2, 65.0, 39.6, 26.3, 23.8, 20.1, 11.7.

Compound 44 was prepared with a yield of 90.0%.

$^1$H NMR (500 MHz, Chloroform-d) δ 7.45 (d, J=7.5 Hz, 1H), 7.27-7.24 (m, 2H), 7.23 (s, 1H), 6.85 (s, 1H), 6.31 (d, J=2.0 Hz, 1H), 5.71 (d, J=1.8 Hz, 1H), 5.63 (d, J=6.7 Hz, 1H), 5.01 (s, 2H), 3.31 (ddd, J=9.6, 6.8, 4.9 Hz, 1H), 2.77-2.69 (m, 1H), 2.53 (ddd, J=16.3, 9.6, 4.4 Hz, 1H), 2.38 (s, 3H), 2.34 (s, 3H), 2.26 (s, 3H), 1.97 (ddd, J=13.5, 10.9, 4.7 Hz, 1H), 1.82 (dtd, J=13.9, 9.6, 4.4 Hz, 1H).

$^{13}$C NMR (125 MHz, Chloroform-d) δ 170.5, 155.2, 140.2, 136.6, 135.4, 134.1, 130.7, 130.4, 128.6, 128.4, 128.2, 126.3, 126.1, 121.5, 114.9, 75.3, 69.2, 39.6, 26.3, 23.8, 20.2, 19.0, 11.7.

Compound 45 was prepared with a yield of 64.9%.

$^1$H NMR (500 MHz, Chloroform-d) δ 7.71 (d, J=8.3 Hz, 2H), 7.18 (d, J=8.4 Hz, 2H), 6.75 (s, 1H), 6.30 (d, J=2.0 Hz, 1H), 5.71 (d, J=1.8 Hz, 1H), 5.62 (d, J=6.7 Hz, 1H), 5.00 (s, 2H), 3.31 (ddd, J=9.5, 6.9, 4.9 Hz, 1H), 2.71 (ddd, J=16.4, 6.1, 4.5 Hz, 1H), 2.51 (ddd, J=16.3, 9.4, 4.4 Hz, 1H), 2.35 (s, 3H), 2.22 (s, 3H), 1.96 (ddd, J=13.5, 11.0, 4.7 Hz, 1H), 1.82 (dtd, J=13.8, 9.6, 4.4 Hz, 1H).

$^{13}$C NMR (125 MHz, Chloroform-d) δ 170.4, 154.8, 140.1, 137.8(2C), 137.3, 134.2, 130.8, 129.1(2C), 128.9, 126.3, 121.5, 115.1, 93.4, 75.2, 70.0, 39.6, 26.3, 23.8, 20.1, 11.7.

Compound 45 was prepared with a yield of 64.9%.

$^1$H NMR (500 MHz, Chloroform-d) δ 7.71 (d, J=8.3 Hz, 2H), 7.18 (d, J=8.4 Hz, 2H), 6.75 (s, 1H), 6.30 (d, J=2.0 Hz, 1H), 5.71 (d, J=1.8 Hz, 1H), 5.62 (d, J=6.7 Hz, 1H), 5.00 (s, 2H), 3.31 (ddd, J=9.5, 6.9, 4.9 Hz, 1H), 2.71 (ddd, J=16.4, 6.1, 4.5 Hz, 1H), 2.51 (ddd, J=16.3, 9.4, 4.4 Hz, 1H), 2.35 (s, 3H), 2.22 (s, 3H), 1.96 (ddd, J=13.5, 11.0, 4.7 Hz, 1H), 1.82 (dtd, J=13.8, 9.6, 4.4 Hz, 1H).

$^{13}$C NMR (125 MHz, Chloroform-d) δ 170.4, 154.8, 140.1, 137.8(2C), 137.3, 134.2, 130.8, 129.1(2C), 128.9, 126.3, 121.5, 115.1, 93.4, 75.2, 70.0, 39.6, 26.3, 23.8, 20.1, 11.7.

Compound 46 was prepared with a yield of 79.5%.

$^1$H NMR (500 MHz, Chloroform-d) δ 7.51 (d, J=7.4 Hz, 1H), 7.33-7.27 (m, 1H), 7.00 (t, J=7.5 Hz, 1H), 6.91 (d, J=8.2 Hz, 1H), 6.85 (s, 1H), 6.30 (d, J=2.0 Hz, 1H), 5.71 (d, J=1.7 Hz, 1H), 5.63 (d, J=6.7 Hz, 1H), 5.09 (s, 2H), 3.87 (s, 3H), 3.30 (ddd, J=9.6, 6.8, 4.9 Hz, 1H), 2.75-2.68 (m, 1H), 2.56-2.48 (m, 1H), 2.38 (s, 3H), 2.23 (s, 3H), 1.96 (ddd, J=13.5, 10.9, 4.8 Hz, 1H), 1.82 (dt, J=13.6, 4.7 Hz, 1H).

¹³C NMR (125 MHz, Chloroform-d) δ 170.5, 156.8, 155.3, 140.3, 134.1, 130.5, 128.8, 128.5, 128.3, 126.3, 126.1, 121.4, 120.8, 115.3, 110.2, 75.3, 65.8, 55.5, 39.6, 29.8, 26.4, 20.1, 11.7.

Compound 47 was prepared with a yield of 86.1%.

¹H NMR (500 MHz, Chloroform-d) δ 7.79 (s, 1H), 7.66 (d, J=7.9 Hz, 1H), 7.41 (d, J=7.7 Hz, 1H), 7.12 (t, J=7.8 Hz, 1H), 6.76 (s, 1H), 6.30 (d, J=2.0 Hz, 1H), 5.71 (d, J=1.8 Hz, 1H), 5.62 (d, J=6.7 Hz, 1H), 4.99 (s, 2H), 3.31 (dtd, J=9.5, 4.9, 2.9 Hz, 1H), 2.71 (ddd, J=16.4, 6.1, 4.5 Hz, 1H), 2.52 (ddd, J=16.2, 9.4, 4.4 Hz, 1H), 2.36 (s, 3H), 2.23 (s, 3H), 1.97 (ddd, J=13.5, 11.0, 4.7 Hz, 1H), 1.82 (dtd, J=13.8, 9.6, 4.4 Hz, 1H).

¹³C NMR (125 MHz, Chloroform-d) δ 170.4, 154.8, 140.1, 140.0, 137.0, 136.1, 134.2, 130.8, 130.4, 129.0, 126.4, 126.3, 121.5, 115.2, 94.5, 75.2, 69.7, 39.6, 26.3, 23.8, 20.1, 11.7.

Compound 48 was prepared with a yield of 77.3%.

¹H NMR (500 MHz, Chloroform-d) δ 8.75 (s, 1H), 7.81 (d, J=7.0 Hz, 1H), 7.61 (d, J=7.5 Hz, 1H), 7.27 (d, J=8.2 Hz, 1H), 6.77 (s, 1H), 6.30 (s, 1H), 5.73 (d, J=15.6 Hz, 1H), 5.60 (d, J=6.5 Hz, 1H), 5.27 (d, J=12.2 Hz, 2H), 3.33 (s, 1H), 2.71 (s, 1H), 2.52 (s, 1H), 2.32 (s, 3H), 2.23 (s, 3H), 1.97 (s, 1H), 1.82 (s, 1H).

Compound 49 was prepared with a yield of 74.1%.

¹H NMR (500 MHz, Chloroform-d) δ 7.68 (s, 1H), 7.60 (s, 1H), 7.46-7.43 2H), 7.39 (t, J=7.5 Hz, 2H), 7.33 (t, J=7.3 Hz, 1H), 6.81 (s, 1H), 6.31 (d, J=2.0 Hz, 1H), 5.71 (d, J=1.8 Hz, 1H), 5.63 (d, J=6.7 Hz, 1H), 5.06 (s, 2H), 3.31 (dtd, J=9.6, 4.9, 2.9 Hz, 1H), 2.72 (ddd, J=16.4, 6.1, 4.5 Hz, 1H), 2.52 (ddd, J=16.3, 9.5, 4.4 Hz, 1H), 2.37 (s, 3H), 2.23 (s, 3H), 2.00-1.93 (m, 1H), 1.82 (dtd, J=13.8, 9.6, 4.4 Hz, 1H).

¹³C NMR (125 MHz, Chloroform-d) δ 170.4, 155.1, 140.2, 139.9, 137.6, 134.1, 130.7, 128.7, 128.7(2C), 127.9, 127.3(2C), 126.3, 122.3, 121.5, 115.2, 75.3, 70.7, 39.6, 26.4, 23.8, 20.1, 11.7.

Compound 50 was prepared with a yield of 93.0%.

¹H NMR (300 MHz, Chloroform-d) δ 7.59 (2H, d, J=7.9 Hz), 7.36 (1H, m), 7.19 (1H, m), 6.80 (1H, s), 6.31 (1H, s), 5.72 (1H, s), 5.63 (1H, d, J=6.7 Hz), 5.10 (2H, s), 3.28-3.35 (1H, m), 2.66-2.81 (1H, m), 2.43-2.60 (1H, m), 2.39 (3H, s), 2.24 (3H, s), 1.91-2.09 (1H, m), 1.70-1.91 (1H, m).

¹³C NMR (125 MHz, Chloroform-d) δ 170.3, 154.6, 140.0, 136.7, 134.1, 132.5, 130.6, 129.1, 128.8, 128.7, 126.1, 122.1, 121.3, 114.9, 75.1, 69.8, 53.4, 39.4, 26.1, 23.6, 20.0, 11.6.

ESIMS: m/z 381.2 [M+H]⁺.

Compound 51 was prepared with a yield of 93.2%.

¹H NMR (300 MHz, Chloroform-d) δ 7.87 (1H, d, J=7.6 Hz), 7.55 (1H, d, J=7.6 Hz), 7.39 (1H, m), 7.03 (1H, m), 6.79 (1H, s), 6.31 (1H, d, J=1.7 Hz), 5.72 (1H, d, J=1.7 Hz), 5.63 (1H, d, J=6.7 Hz), 5.01 (2H, s), 3.28-3.35 (1H, m), 2.68-2.77 (1H, m), 2.45-2.59 (1H, m), 2.39 (3H, s), 2.24 (3H, s), 1.92-2.02 (1H, m), 1.77-1.88 (1H, m).

¹³C NMR (125 MHz, Chloroform-d) δ 170.3, 154.5, 140.0, 139.5, 139.2, 134.1, 130.6, 129.4, 128.8, 128.5, 128.4, 126.1, 121.3, 114.9, 97.0, 75.1, 74.4, 39.4, 26.2, 23.6, 20.0, 11.7.

ESIMS: m/z 461.0 [M+H]⁺.

Compound 52 was prepared with a yield of 89.6%.

¹H NMR (300 MHz, Chloroform-d) δ 7.79 (1H, d, J=7.8 Hz), 7.70 (1H, d, J=7.8 Hz), 7.59 (1H, m), 7.42 (1H, m), 6.75 (1H, s), 6.31 (1H, s), 5.72 (1H, s), 5.64 (1H, d, J=6.7 Hz), 5.25 (2H, s), 3.28-3.35 (1H, m), 2.67-2.76 (1H, m), 2.44-2.58 (1H, m), 2.39 (3H, s), 2.22 (3H, s), 1.92-2.02 (1H, m), 1.77-1.88 (1H, m).

¹³C NMR (125 MHz, Chloroform-d) δ 170.2, 154.5, 140.0, 136.1, 134.1, 132.2, 130.7, 128.9, 128.4, 127.5, 127.2, 126.0, 125.7, 125.5, 121.4, 114.8, 75.1, 66.4, 39.4, 26.1, 23.6, 20.0, 11.6.

ESIMS: m/z 403.0 [M+H]⁺.

Compound 53 was prepared with a yield of 81.5%.

¹H NMR (300 MHz, Chloroform-d) δ 7.73 (1H, s), 7.69 (1H, d, J=7.6 Hz), 7.63 (1H, d, J=7.6 Hz), 7.51 (1H, m), 6.75 (1H, s), 6.31 (1H, s), 5.72 (1H, s), 5.63 (1H, d, J=6.8 Hz), 5.08 (2H, s), 3.29-3.36 (1H, m), 2.65-2.80 (1H, m), 2.42-2.59 (1H m), 2.36 (3H, s), 2.23 (3H, s), 1.90-2.05 (1H, m), 1.79-1.88 (1H, m).

¹³C NMR (125 MHz, Chloroform-d) δ 170.2, 154.4, 139.8, 134.1, 131.5, 131.3, 130.9, 130.4, 129.4, 129.2, 126.1, 121.4, 118.7, 114.9, 112.7, 75.0, 69.3, 53.4, 39.4, 26.1, 23.6, 20.0, 11.6.

ESIMS: m/z 382.1 [M+Na]⁺.

Compound 54 was prepared with a yield of 67.6%.

¹H NMR (300 MHz, Chloroform-d) δ 7.19-7.35 (3H, m), 7.14 (1H, d, J=6.8 Hz), 6.81 (1H, s), 6.30 (1H, s), 5.71 (1H, s), 5.63 (1H, d, I=6.7 Hz), 5.02 (2H, s), 3.27-3.34 (1H, m), 2.67-2.76 (1H, m), 2.43-2.61 (1H, m), 2.38 (3H, s), 2.37 (3H, s), 2.23 (3H, s), 1.89-2.08 (1H, m), 1.77-1.83 (1H, m).

¹³C NMR (125 MHz, Chloroform-d) δ 170.3, 155.1, 140.0, 138.2, 137.4, 133.9, 130.5, 128.5, 128.4, 127.9, 126.2, 124.2, 121.3, 115.1, 75.1, 70.6, 53.4, 39.4, 26.2, 23.6, 21.4, 19.9, 11.6.

ESIMS: m/z 371.0 [M+Na]⁺.

Compound 55 was prepared with a yield of 82.1%.

¹H NMR (300 MHz, Chloroform-d) δ 7.07-7.14 (2H, m), 6.91 (1H, dd, J=6.2, 3.4 Hz), 6.87 (1H, s), 6.30 (1H, d, J=1.8 Hz), 5.71 (1H, d, J=1.8 Hz), 5.62 (1H, d, J=6.7 Hz), 5.09 (2H, s), 3.89 (3H, s), 3.88 (3H, s), 3.22-3.37 (1H, m), 2.76-2.68 (1H, m), 2.43-2.62 (1H, m), 2.35 (3H, s), 2.24 (3H, s). 1.87-1.99 (1H, m), 1.78-1.87 (1H, m).

¹³C NMR (125 MHz, Chloroform-d) δ 170.3, 155.0, 152.5, 146.8, 140.1, 134.0, 130.4, 128.4, 126.0, 124.1, 121.2, 120.7, 114.9, 112.0, 75.1, 65.6, 61.0, 55.8, 39.5, 31.5, 26.2, 22.6, 19.9, 11.6.

ESIMS: m/z 417.0 [M+Na]⁺.

Compound 56 was prepared with a yield of 97.1%.

¹H NMR (300 MHz, Chloroform-d) δ 7.51 (2H, d, J=7.8 Hz), 7.31 (2H, d, J=7.8 Hz), 6.76 (1H, s), 6.30 (1H, s), 5.71 (1H, s), 5.62 (1H, d, J=6.7 Hz), 5.01 (2H, s), 3.28-3.34 (1H, m), 2.65-2.77 (1H, m), 2.44-2.57 (1H, m), 2.35 (3H, s), 2.22 (3H, s), 1.92-2.01 (1H, m), 1.73-1.89 (1H, m).

¹³C NMR (125 MHz, Chloroform-d) δ 170.2, 154.6, 139.9, 136.5, 134.0, 131.6 (2C), 130.7, 128.79, 128.75 (2C), 126.1, 121.6, 121.4, 115.0, 75.0, 69.8, 39.4, 26.1, 23.6, 20.0, 11.6.

ESIMS: m/z 847.2 [2M+Na]⁺.

Compound 57 was prepared with a yield of 79.8%.

¹H NMR (300 MHz, Chloroform-d) δ 7.47 (2H, d, J=8.5 Hz), 7.24 (2H, d, J=8.5 Hz), 6.78 (1H, s), 6.30 (1H, s), 5.71 (1H, s), 5.62 (1H, d, J=6.7 Hz), 5.05 (2H, s), 3.28-3.35 (1H, m), 2.67-2.74 (1H, m), 2.52-2.56 (1H, m), 2.36 (3H, s), 2.23 (3H, s), 1.94-2.00 (1H, m), 1.79-1.89 (1H, m).

¹³C NMR (125 MHz, Chloroform-d) δ 170.2, 154.7, 148.7, 139.9, 136.1, 134.0, 130.7, 128.8, 128.4(2C), 126.1, 121.3, 121.0(2C), 119.4, 114.9, 75.0, 69.6, 39.4, 26.1, 23.6, 19.9, 11.5.

ESIMS: m/z 419.0 [M+H]⁺.

Compound 58 was prepared with a yield of 85.4%.

¹H NMR (500 MHz, Chloroform-d) δ 7.80-7.69 (m, 2H), 7.46 (t, J=7.5 Hz, 2H), 7.38 (t, J=7.3 Hz, 1H), 6.81 (s, 1H), 6.36 (d, J=2.0 Hz, 1H), 5.81 (d, J=1.8 Hz, 1H), 5.63 (d, J=6.7 Hz, 1H), 5.06 (s, 2H), 3.31 (dtd, J=9.6, 4.9, 2.9 Hz, 1H), 2.72

(ddd, J=16.4, 6.1, 4.5 Hz, 1H), 2.52 (ddd, J=16.3, 9.5, 4.4 Hz, 1H), 2.37 (s, 3H), 2.23 (s, 3H), 2.00-1.93 (m, 1H), 1.82 (dtd, J=13.8, 9.6, 4.4 Hz, 1H).

$^{13}$C NMR (125 MHz, Chloroform-d) δ 170.4, 156.1, 146.2, 137.6, 134.1, 130.7, 129.7, 128.7, 128.7(2C), 127.9, 127.3(2C), 126.3, 121.5, 115.2, 75.3, 70.7, 39.6, 26.4, 23.8, 20.1, 11.7.

EXAMPLE 4

Preparation of (3R/S,3aS,9bR)-8-(2-bromobenzyloxy)-3-dimethylaminomethyl-6,9-dimethyl-3a, 4,5, 9b-tetrahydronaphtho [1,2-b]furan-2(3H)-one (Compound 59)

1.0 g of (3a S,9bR)-8-(2-bromobenzyloxy)-6,9-dimethyl-3-methylene-3a,4,5,9b-tetrahydronaphtho [1,2-b]furan-2 (3H)-one (2.43 mmol, 1.0 eq) and 0.3 g of dimethylamine hydrochloride (3.64 mmol, 1.5 eq) were dissolved in 20 mL of ethanol. The reaction mixture was dropwise added with 0.37 g of triethylamine (3.64 mmol, 0.51 mL) at 0° C., naturally heated to normal temperature and stirred. After the compound 51 was confirmed by TLC to be completely consumed, the reaction mixture was evaporated under vacuum at low temperature to remove ethanol and extracted with water and dichloromethane. The organic phase was washed with saturated brine, dried with anhydrous Na$_2$SO$_4$ and purified by column chromatography to give 1.1 g of a white solid (3R/S,3aS,9bR)-8-(2-bromobenzyloxy)-3-dimethylaminomethyl-6,9-dimethyl-3a,4,5,9b-tetrahydronaphtho [1,2-b]furan-2(3H)-one with a yield of 99%, where a mixture of PE and EA in a ratio of 20:1 was used as an eluent.

$^1$H NMR (500 MHz, Chloroform-d) δ 7.58 (t, J=7.1 Hz, 2H), 7.35 (t, J=7.2 Hz, 1H), 7.18 (t, J=7.2 Hz, 1H), 6.81 (s, 1H), 5.40 (d, J=3.4 Hz, 1H), 5.09 (s, 2H), 3.24-3.10 (m, 1H), 2.84 (d, J=16.2 Hz, 1H), 2.77-2.59 (m, 2H), 2.45 (dd, J=8.1, 21.4 Hz, 1H), 2.37 (s, 3H), 2.34 (s, 6H), 2.24 (s, 3H), 2.05 (d, J=11.7 Hz, 1H), 1.40-1.25 (m, 1H).

$^{13}$C NMR (125 MHz, CDCl$_3$) δ 177.0, 154.4, 136.7, 134.2, 132.5, 130.1, 129.2, 129.1, 128.7, 127.6, 125.8, 122.1, 115.0, 75.9, 69.8, 54.6, 45.6, 44.3, 38.3, 25.1, 20.0, 19.3, 11.4.

Compounds 60-69 were synthesized according to the process in Example 4.

Compound 60 was prepared with a yield of 92.8%.

$^1$H NMR (500 MHz, CDCl$_3$) δ 7.58-7.54 (m, 2H), 7.33 (t, J=7.6 Hz, 1H), 7.21-7.18 (m, 1H), 6.79 (s, 1H), 5.38 (d, J=4.4 Hz, 1H), 5.09 (s, 2H), 3.15 (q, J=7.2 Hz, 1H), 3.04-2.98 (m, 1H), 2.82 (d, J=15.9 Hz, 2H), 2.72-2.63 (m, 2H), 2.50 (s, 3H), 2.35 (s, 3H), 2.23 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.8, 154.3, 136.8, 134.2, 132.5, 129.9, 129.1, 128.9, 128.6, 127.6, 125.8, 122.1, 115.0, 75.9, 69.8, 47.5, 45.7, 38.4, 36.6, 25.1, 19.9, 19.6, 11.4.

Compound 61 was prepared with a yield of 91.1%.

$^1$H NMR (500 MHz, CDCl$_3$) δ 7.59-7.55 (m, 2H), 7.34 (t, J=7.6 Hz, 1H), 7.20-7.16 (m, 1H), 6.80 (s, 1H), 5.39 (d, J=4.4 Hz, 1H), 5.08 (s, 2H), 3.14 (q, J=7.2 Hz, 1H), 3.06-2.99 (m, 1H), 2.83 (d, J=15.9 Hz, 2H), 2.71-2.62 (m, 2H), 2.50 (s, 3H), 2.35 (s, 3H), 2.23 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.6, 154.4, 136.6, 134.2, 132.5, 129.9, 129.1, 128.9, 128.6, 127.6, 125.8, 122.1, 115.0, 75.9, 69.8, 47.5, 45.7, 38.4, 36.6, 25.1, 19.9, 19.6, 11.4.

Compound 62 was prepared with a yield of 92.8%.

$^1$H NMR (500 MHz, Chloroform-d) δ 7.59 (t, J=7.1 Hz, 2H), 7.36 (t, J=7.2 Hz, 1H), 7.19 (t, J=7.2 Hz, 1H), 6.83 (s, 1H), 5.38 (d, J=4.4 Hz, 1H), 5.08 (s, 2H), 3.14 (q, J=7.2 Hz, 1H), 3.06-2.99 (m, 1H), 2.83 (d, J=15.9 Hz, 2H), 2.71-2.62 (m, 2H), 2.51 (s, 3H), 2.35 (s, 3H), 2.23 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.6, 154.4, 138.6, 134.2, 132.5, 129.9, 129.1, 128.9, 128.6, 127.6, 125.8, 122.1, 115.0, 75.9, 69.8, 47.5, 45.7, 38.5, 36.6, 25.1, 19.9, 19.6, 11.4.

Compound 63 was prepared with a yield of 89.5%.

$^1$H NMR (500 MHz, CDCl$_3$) δ 7.62-7.56 (m, 2H), 7.36 (td, J=1.1, 7.6 Hz, 1H), 7.19 (td, J=1.6, 7.9 Hz, 1H), 6.81 (s, 1H), 5.39 (d, J=4.5 Hz, 1H), 5.11 (s, 2H), 3.17 (ddd, J=4.2, 6.5, 10.9 Hz, 1H), 2.98-2.91 (m, 1H), 2.85 (ddd, J=2.3, 4.5, 16.7 Hz, 1H), 2.79 (dd, J=4.2, 12.7 Hz, 1H), 2.76-2.70 (m, 1H), 2.69-2.63 (m, 2H), 2.59-2.53 (m, 2H), 2.51-2.42 (m, 1H), 2.36 (s, 3H), 2.24 (s, 3H), 2.12-2.05 (m, 1H), 1.83 (t, J=6.4 Hz, 4H), 1.34 (qd, J=4.6, 13.1 Hz, 1H).

$^{13}$C NMR (125 MHz, CDCl$_3$) δ 177.0, 154.4, 136.7, 134.2, 132.5, 130.2, 129.2, 129.1, 128.7, 127.6, 125.9, 122.1, 115.0, 75.8, 69.9, 54.3, 51.1, 45.6, 38.4, 25.1, 23.6, 19.9, 19.4, 11.4.

Compound 64 was prepared with a yield of 90.2%.

$^1$H NMR (500 MHz, CDCl$_3$) δ 7.59 (d, J=8.0 Hz, 2H), 7.39-7.32 (m, 1H), 7.20 (td, J=1.5, 7.9 Hz, 1H), 6.82 (s, 1H), 5.39 (d, J=4.5 Hz, 1H), 5.11 (s, 2H), 3.81-3.69 (m, 4H), 3.21 (ddd, J=4.5, 6.5, 10.9 Hz, 1H), 2.86 (ddd, J=2.2, 4.3, 16.7 Hz, 1H), 2.81 (dd, J=4.4, 13.1 Hz, 1H), 2.73-2.58 (m, 4H), 2.52-2.42 (m, 3H), 2.36 (s, 3H), 2.25 (s, 3H), 2.06 (dd, J=3.5, 9.3 Hz, 1H), 1.34 (qd, J=4.6, 13.1 Hz, 1H).

$^{13}$C NMR (125 MHz, CDCl$_3$) δ 177.0, 154.4, 136.7, 134.2, 132.5, 130.0, 129.1, 128.7, 127.6, 125.8, 122.1, 115.0, 75.8, 69.9, 66.9, 53.7, 53.7, 43.6, 38.6, 25.2, 19.9, 19.3, 11.4.

Compound 65 was prepared with a yield of 96.3%.

$^1$H NMR (500 MHz, CDCl$_3$) δ 7.62-7.56 (m, 2H), 7.35 (td, J=1.1, 7.6 Hz, 1H), 7.19 (td, J=1.6, 7.9 Hz, 1H), 6.81 (s, 1H), 5.38 (d, J=4.5 Hz, 1H), 5.10 (s, 2H), 3.72 (q, J=7.0 Hz, 1H), 3.20 (ddd, J=4.4, 6.5, 10.8 Hz, 1H), 3.00 (d, J=10.3 Hz, 1H), 2.88-2.80 (m, 2H), 2.76 (dd, J=4.3, 13.2 Hz, 1H), 2.71-2.64 (m, 2H), 2.45 (ddd, J=4.7, 13.1, 17.1 Hz, 1H), 2.36 (s, 3H), 2.24 (s, 3H), 2.16 (td, J=2.5, 11.6 Hz, 1H), 2.10-2.03 (m, 1H), 1.96 (td, J=2.4, 11.6 Hz, 1H), 1.68-1.60 (m, 2H), 1.43-1.35 (m, 1H), 1.34-1.28 (m, 1H), 1.24-1.17 (m, 1H), 0.94 (d, J=6.5 Hz, 3H).

$^{13}$C NMR (125 MHz, CDCl$_3$) δ 177.4, 154.4, 136.7, 134.2, 132.5, 130.2, 129.2, 129.0, 128.7, 127.6, 125.8, 122.1, 115.0, 75.8, 69.9, 55.4, 53.5, 52.8, 44.1, 38.7, 34.4, 34.2, 30.7, 25.2, 21.9, 19.9, 19.3, 11.4.

Compound 66 was prepared with a yield of 93.1%.

$^1$H NMR (500 MHz, CDCl$_3$) δ 7.59-7.53 (m, 1H), 7.33-7.28 (m, 1H), 7.18 (t, J=7.5 Hz, 1H), 7.12-7.06 (m, 1H), 6.82 (s, 1H), 5.38 (d, J=4.5 Hz, 1H), 5.11 (s, 2H), 3.81-3.69 (m, 4H), 3.21 (ddd, J=4.5, 6.5, 10.9 Hz, 1H), 2.86 (ddd, J=2.2, 4.3, 16.7 Hz, 1H), 2.81 (dd, J=4.4, 13.1 Hz, 1H), 2.73-2.58 (m, 4H), 2.52-2.42 (m, 3H), 2.36 (s, 3H), 2.25 (s, 3H), 2.06 (dd, J=3.5, 9.3 Hz, 1H), 1.34 (qd, J=4.6, 13.1 Hz, 1H).

$^{13}$C NMR (125 MHz, CDCl$_3$) δ 177.1, 154.4, 136.7, 134.2, 132.5, 130.0, 129.1, 128.7, 127.6, 125.8, 122.1, 115.0, 75.8, 69.9, 66.9, 53.7, 53.7, 43.6, 38.6, 25.2, 19.9, 19.5, 11.6.

Compound 67 was prepared with a yield of 91.0%.

$^1$H NMR (500 MHz, CDCl$_3$) δ 7.61-7.58 (m, 2H), 7.36 (td, J=1.1, 7.6 Hz, 1H), 7.18 (td, J=1.6, 7.9 Hz, 1H), 6.80 (s,

1H), 5.39 (d, J=4.5 Hz, 1H), 5.10 (s, 2H), 3.72 (q, J=7.0 Hz, 1H), 3.20 (ddd, J=4.4, 6.5, 10.8 Hz, 1H), 3.00 (d, J=10.3 Hz, 1H), 2.88-2.80 (m, 2H), 2.74 (dd, J=4.3, 13.2 Hz, 1H), 2.71-2.64 (m, 2H), 2.45 (ddd, J=4.7, 13.1, 17.1 Hz, 1H), 2.36 (s, 3H), 2.24 (s, 3H), 2.16 (td, J=2.5, 11.6 Hz, 1H), 2.10-2.03 (m, 1H), 1.96 (td, J=2.4, 11.6 Hz, 1H), 1.68-1.60 (m, 2H), 1.43-1.35 (m, 1H), 1.34-1.28 (m, 1H), 1.24-1.17 (m, 1H).

$^{13}$C NMR (125 MHz, CDCl$_3$) δ 177.5, 154.5, 136.7, 134.3, 132.5, 130.2, 129.2, 129.0, 128.7, 127.6, 125.8, 122.1, 115.0, 75.8, 69.9, 56.4, 53.5, 52.8, 44.1, 38.7, 34.4, 34.2, 30.7, 25.2, 21.9, 19.3, 11.4.

Compound 68 was prepared with a yield of 95.2%.

$^1$H NMR (500 MHz, CDCl$_3$) δ 7.59-7.55 (m, 2H), 7.37-7.29 (m, 5H), 7.34 (t, J=7.6 Hz, 1H), 7.20-7.16 (m, 1H), 6.80 (s, 1H), 5.39 (d, J=4.4 Hz, 1H), 5.08 (s, 2H), 3.25 (s, 2H), 3.14 (q, J=7.2 Hz, 1H), 3.06-2.99 (m, 1H), 2.83 (d, J=15.9 Hz, 2H), 2.71-2.62 (m, 2H), 2.35 (s, 3H), 2.23 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.6, 154.4, 136.6, 134.2, 132.5, 129.9, 129.1, 128.9, 128.6, 128.5(2C), 127.6, 127.3(2C), 126.8, 125.8, 122.1, 115.0, 75.9, 69.8, 52.6, 47.5, 38.4, 36.6, 25.1, 19.9, 19.6, 11.4.

Compound 69 was prepared with a yield of 93.6%.

$^1$H NMR (500 MHz, CDCl$_3$) δ 7.58-7.52 (m, 1H), 7.35-7.29 (m, 1H), 7.19 (t, J=7.5 Hz, 1H), 7.11-7.08 (m, 1H), 6.81 (s, 1H), 5.39 (d, J=4.5 Hz, 1H), 5.11 (s, 2H), 4.13 (m, 2H), 3.17 (ddd, J=4.2, 6.5, 10.9 Hz, 1H), 2.98-2.91 (m, 1H), 2.85 (ddd, J=2.3, 4.5, 16.7 Hz, 1H), 2.79 (dd, J=4.2, 12.7 Hz, 1H), 2.78-2.73 (m, 1H), 2.76-2.70 (m, 1H), 2.59-2.53 (m, 2H), 2.51-2.42 (m, 1H), 2.36 (s, 3H), 2.24 (s, 3H), 2.12-2.05 (m, 1H), 1.83 (t, J=6.4 Hz, 4H), 1.34 (qd, J=4.6, 13.1 Hz, 1H), 1.21 (t, 3H).

$^{13}$C NMR (125 MHz, CDCl$_3$) δ 177.0, 173.5, 154.4, 136.7, 134.2, 132.5, 130.2, 129.2, 129.1, 128.7, 127.6, 125.9, 122.1, 115.0, 75.8, 71.9, 69.9 61.3, 51.1, 45.6, 38.4, 25.1, 23.6, 19.9, 19.4, 14.1, 11.6.

EXAMPLE 5

Preparation of (3R/S,3aS,9bR)-8-(2-bromobenzyloxy)-3-dimethylaminomethyl-6,9-dimethyl-3a, 4,5, 9b-tetrahydronaphtho [1,2-b]furan-2(3H)-one hydrochloride (Compound 70)

1.0 g of compound 59 (2.18 mmol, 1.0 eq) was dissolved in 20 mL of dichloromethane, to which the same equivalent of hydrochloric acid was dropwise added at room temperature. The reaction mixture was reacted under stirring at room temperature, and the dropwise addition of the aqueous hydrochloric acid solution was stopped when the reaction mixture had pH of 4-5. The aqueous phase was collected and lyophilized to give 0.99 g of compound 70 with a yield of 92%.

$^1$H NMR (500 MHz, Chloroform-d) δ 7.58 (t, J=7.1 Hz, 2H), 7.35 (t, J=7.2 Hz, 1H), 7.18 (t, J=7.2 Hz, 1H), 6.81 (s, 1H), 5.40 (d, J=3.4 Hz, 1H), 5.09 (s, 2H), 3.74 (d, J=16.2 Hz, 1H), 3.46 (dd, J=8.1, 21.4 Hz, 1H), 3.24-3.10 (m, 1H), 2.78-2.62 (m, 2H), 2.74 (s, 6H), 2.37 (s, 3H), 2.24 (s, 3H), 2.05 (d, J=11.7 Hz, 1H), 1.40-1.25 (m, 1H).

$^{13}$C NMR (125 MHz, CDCl$_3$) δ 177.0, 154.4, 136.7, 134.2, 132.5, 130.1, 129.2, 129.1, 128.7, 127.6, 125.8, 122.1, 115.0, 75.9, 69.8, 52.8, 44.3, 43.6, 38.3, 25.1, 20.0, 19.3, 11.5.

Compounds 71-72 in Table 1 were synthesized according to the process in Example 5.

Compound 71 was prepared with a yield of 95.0%.

$^1$H NMR (500 MHz, Chloroform-d) δ 16.32 (s, 1H), 7.58 (t, J=7.1 Hz, 2H), 7.35 (t, J=7.2 Hz, 1H), 7.31 (s, 1H), 7.18 (t, J=7.2 Hz, 1H), 6.81 (s, 1H), 6.28 (s, 1H), 5.40 (d, J=3.4 Hz, 1H), 5.09 (s, 2H), 3.74 (d, J=16.2 Hz, 1H), 3.46 (dd, J=8.1, 21.4 Hz, 1H), 3.24-3.10 (m, 1H), 2.78-2.62 (m, 2H), 2.74 (s, 6H), 2.37 (s, 3H), 2.24 (s, 3H), 2.05 (d, J=11.7 Hz, 1H), 1.40-1.25 (m, 1H).

$^{13}$C NMR (125 MHz, CDCl$_3$) δ 177.0, 170.4, 167.4, 154.4, 138.9, 136.7, 134.5, 134.2, 132.5, 130.1, 129.2, 129.1, 128.7, 127.6, 125.8, 122.1, 115.0, 75.9, 69.8, 52.8, 44.3, 43.6, 38.3, 25.1, 20.0, 19.3, 11.5.

Compound 72 was prepared with a yield of 95.0%.

$^1$H NMR (500 MHz, Chloroform-d) δ 9.93 (s,1H), 7.58 (t, J=7.1 Hz, 2H), 7.35 (t, J=7.2 Hz, 1H), 7.18 (t, J=7.2 Hz, 1H), 6.81 (s, 1H), 5.40 (d, J=3.4 Hz, 1H), 5.09 (s, 2H), 3.74 (d, J=16.2 Hz, 1H), 3.46 (dd, J=8.1, 21.4 Hz, 1H), 3.32(s,3H), 3.24-3.10 (m, 1H), 2.78-2.62 (m, 2H), 2.74 (s, 6H), 2.37 (s, 3H), 2.24 (s, 3H), 2.05 (d, J=11.7 Hz, 1H), 1.40-1.25 (m, 1H).

$^{13}$C NMR (125 MHz, CDCl$_3$) δ 177.0, 154.4, 136.7, 134.2, 132.5, 130.1, 129.2, 129.1, 128.7, 127.6, 125.8, 122.1, 115.0, 75.9, 69.8, 52.8, 44.3, 43.6, 39.8, 38.3, 25.1, 20.0, 19.3, 11.5.

Compounds 73-75 in Table 1 were synthesized according to the process in Example 4.

Compound 73 was prepared with a yield of 95.0%.

$^1$H NMR (500 MHz, CDCl$_3$) δ 7.59-7.55 (m, 2H), 7.34 (t, 7.6 Hz, 1H), 7.20-7.16 (m, 1H), 6.80 (s, 1H), 5.39 (d, J=4.4 Hz, 1H), 5.08 (s, 2H), 3.93 (s, 3H), 3.14 (q, J=7.2 Hz, 1H), 3.06-2.99 (m, 1H), 2.83 (d, J=15.9 Hz, 2H), 2.78-2.66 (m, 2H), 2.50 (s, 3H), 2.35 (s, 3H), 2.16 (d, J=7.8 Hz, 1H), 1.93-1.86 (m, 1H), 1.37 (dd, J=4.7 12.9 Hz, 1H).

$^{13}$C NMR (125 MHz, CDCl$_3$) δ 177.6, 154.4, 136.6, 134.2, 132.5, 129.9, 129.1, 128.9, 128.6, 127.6, 125.8, 122.1, 115.0, 75.9, 69.8, 47.5, 45.7, 38.4, 36.6, 25.1, 19.9, 19.6, 11.4.

Compound 74 was prepared with a yield of 95.0%.

$^1$H NMR (500 MHz, CDCl$_3$) δ 7.59-7.55 (m, 2H), 7.34 (t, J=7.6 Hz, 1H), 7.29 (m, 4H), 7.20-7.16 (m, 1H), 7.18 (m, 1H), 6.80 (s, 1H), 5.39 (d, J=4.4 Hz, 1H), 5.08 (s, 2H), 3.14 (q, J=7.2 Hz, 1H), 3.06-2.99 (m, 1H), 2.83 (d, J=15.9 Hz, 2H), 2.78-2.66 (m, 2H), 2.50 (s, 3H), 2.35 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.6, 154.4, 136.6, 134.2, 132.5, 129.9, 129.6, 129.1, 128.9, 128.6, 128.3, 127.6, 125.8, 125.2, 122.1, 115.0, 75.9, 69.8, 47.5, 45.7, 38.4, 36.6, 25.1, 19.9, 11.4.

Compound 75 was prepared with a yield of 95.0%.

$^1$H NMR (500 MHz, CDCl$_3$) δ 7.58-7.53 (m, 2H), 7.35-7.29 (m, 5H), 7.33 (t, J=7.6 Hz, 1H), 7.22-7.18 (m, 1H), 6.80 (s, 1H), 5.33 (d, J=4.4 Hz, 1H), 5.03 (s, 2H), 3.25 (s, 2H), 3.14 (q, J=7.2 Hz, 1H), 3.06-2.99 (m, 1H), 2.83 (d, J=15.9 Hz, 2H), 2.71-2.62 (m, 2H), 2.35 (s, 3H), 2.23 (s, 3H), 2.16 (d, J=7.8 Hz, 1H), 1.93-1.86 (m, 1H), 1.37 (dd, J=4.7, 12.9 Hz, 1H).

$^{13}$C NMR (125 MHz, CDCl$_3$) δ 177.6, 154.4, 136.6, 134.2, 132.5, 129.9, 129.1, 128.9, 128.8, 128.3(2C), 127.3(2C), 126.8, 125.8, 122.1, 115.0, 75.9, 69.8, 52.6, 47.5, 38.4, 36.8, 26.1, 19.9, 19.6, 11.8.

EXAMPLE 6

Study on the Therapeutic Effect of the Tetrahydronaphtho [1,2-b]furan-2 (3H)-one Derivative (Compound 59 in Table 1) on Adjuvant-Induced Arthritis in Rats (1) Experimental Animals and Materials Wistar male rats, weighing 160-180 g, were raised in the SPF animal room of Shanghai University of Traditional Chinese Medicine, and employed for experiment following at least one week of culture, where the culture was performed at a temperature of 22+1° C. and a humidity of 55±5% under a 12-h light-dark cycle. The feed and water were sterilized and then freely taken by rats. All experiments were carried out in strict accordance with the relevant regulations for experimental animals.

Bacille Calmette-Guerin (BCG) H37Ra was purchased from Difco Co., Ltd. (US); and the YSL-7A Plethysmometer (paw volume) Meter was produced by the equipment station of Shandong Academy of Medical Sciences.

(2) Experimental Method and Evaluation

The establishment of the adjuvant-induced arthritis rat model and the administration therefor were described performed as follows. Liquid paraffin was sterilized at high temperature and pressure, added with a 10 mg/mL aqueous BCG solution and emulsified under repeated suction to produce a Freund's complete adjuvant (CFA) emulsion. In the experiment, individual rats were sensitized by intradermal injection of 0.1 mL of the CFA emulsion at the left hind paw to induce adjuvant arthritis in the limbs.

The grouping and administration were performed as follows. The male wistar rats were randomly divided into four groups according to weight each for 10 rats.

The rats in the blank control group were treated with 0.3% CMC solution daily by intragastric administration.

The rats in the arthritis solvent control group were similarly treated with 0.3% CMC solution daily by intragastric administration.

Rats from the two administration groups were respectively treated with 5 mg/kg and 20 mg/kg of compound 59 by oral administration once a day.

In addition to the blank control group, the rats in the other three groups were sensitized individually by intramuscular injection of 0.1 mL of an adjuvant containing 10 mg/mL inactivated bacillus strain at the left hind foot pad. From the $10^{th}$ day after the occurrence of arthritis, the rats in the administration groups were orally administered for therapeutic pharmacodynamic observation.

The therapeutic effect was monitored as follows. The rats were observed every day for the development of arthritis symptoms and weighed once every 2-3 days. A 5-level standard scoring system based on the clinical disease index was employed to evaluate the inflammation, where "0": no redness and swelling; "1": redness and swelling at the small toe joints; "2": swelling at the toe joints and toes; "3": swelling at feet below the ankle joint; and "4": swelling at the entire feet including ankle joint. The two hind feet were measured for the volume to evaluate the swelling degree.

(3) EXPERIMENTAL RESULTS

The joints of the extremities began to swell about 10 days after the rats in the model group were injected intradermally with the complete adjuvant at the footpad, and the occurrence rate was up to 100%. The ankle joint at the sensitization side suffered from inflammatory swelling while the ankle joint at the opposite side underwent a secondary autoimmune swelling, which indicated the successful establishment of the adjuvant-induced arthritis rat model. At this time, the degree of the swelling at the two hind feet was measured and scored, and the weight was simultaneously measured.

The weight of individual rats was monitored throughout the experiment, and the results were shown in FIG. 1, which revealed the effect of the daily therapeutic administration of compound 59 on the weight of the rats with adjuvant-induced arthritis. It can be seen from FIG. 1 that the rats in the adjuvant-induced arthritis model group were significantly reduced in weight during the observation, and different doses of the compound 59 (5 mg/kg and 20 mg/kg) showed similar effect on the weight.

Figure 2:
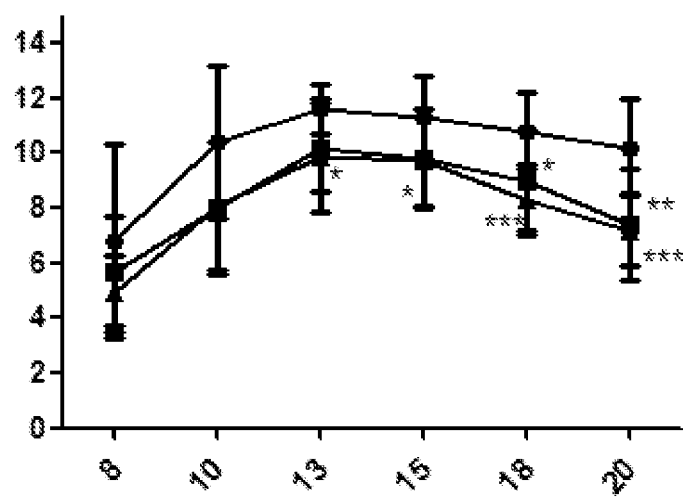
FIG. 2 shows shows the effect of daily therapeutic administration of compound 59 on the disease index of the adjuvant-induced arthritis in rats, where the abscissa and ordinate respectively represent time (day) and rheumatoid arthritis clinical disease index.

During the experiment, the standard score (clinical disease index) for rats from respective groups was recorded to reflect the degree of the arthritis, and the results were shown in FIG. 2, which revealed the effect of the daily therapeutic administration of compound 59 on the disease index of the adjuvant-induced arthritis in rats. Specifically, the rats in the model group presented progressive arthritis, and compared to the model group, the disease index of arthritis in the rats from the compound 59 administration group was significantly lowered (P<0.05).

Figure 3:
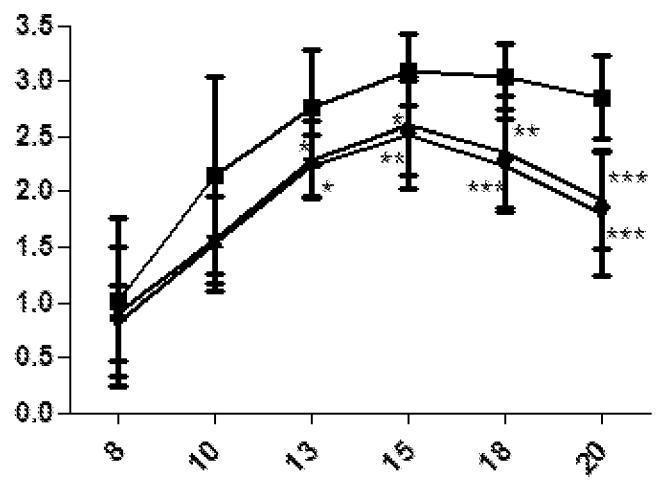
FIG. 3 shows the inhibitory effect of daily therapeutic administration of compound 59 on secondary foot lesions in rats with adjuvant-induced arthritis, where the abscissa and ordinate respectively represent time (day) and foot diameter of rats.

After injected intradermally with the complete adjuvant at the footpad, the rats in the model group suffered from an inflammatory swelling at the ankle joint on the sensitization side and a secondary autoimmune swelling on the opposite side. The effect of the daily therapeutic administration of compound 59 on secondary immune lesions was observed in this experiment, and the results were shown in FIG. 3, which revealed the inhibitory effect of the daily therapeutic administration of compound 59 on secondary foot lesions of the rats with adjuvant-induced arthritis. It can be seen from the results that the rats in the adjuvant-induced arthritis model group underwent significant swelling at the feet during the observation, while compared to the model group, the secondary lesions of the rats in respective compound 59 administration groups were significantly inhibited (P <0.05), alleviating the foot swelling.

Figure 4:
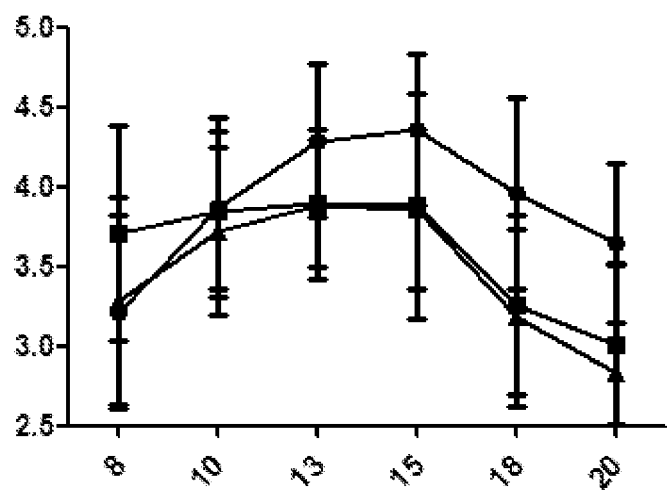
FIG. 4 shows the inhibitory effect of daily therapeutic administration of compound 59 on primary foot lesions in rats with adjuvant-induced arthritis, where the abscissa and ordinate respectively represent time (day) and foot diameter of rats.

After injected intradermally with the complete adjuvant at the footpad, the rats in the model group suffered from an inflammatory swelling at the ankle joint on the sensitization side. The effect of TMX on the sensitized primary foot inflammatory lesions was observed herein, and the results were shown in FIG. 4, which revealed the inhibitory effect of the daily therapeutic administration of compound 59 on primary foot lesions of the rats with adjuvant-induced arthritis. As the results demonstrated, the rats in the adjuvant-induced arthritis model group underwent significant swelling at the feet during the observation, while compared to the model group, the primary lesions of the rats in respective compound 59 administration groups were significantly inhibited (P<0.05), alleviating the foot swelling.

(4) CONCLUSIONS

An adjuvant-induced Wistar male rat arthritis model was established herein, and then the preventive effect of compound 59 on the adjuvant-induced arthritis in rats was investigated. The experimental results confirmed that when it reached the peak of the onset of arthritis, different dosages of compound 59 (5 mg/kg and 20 mg/kg) were administered orally to the arthritic rats once a day, which showed no significant effect on the weight loss but significantly lowered the disease index, alleviating the primary and secondary lesions of arthritis in rats. Therefore, compound 59 of the invention had remarkable therapeutic effect.

It was confirmed by such results that the daily oral administration of tetrahydronaphtho [1,2-b]furan-2(3H)-one derivatives represented by compound 59 showed different degrees of therapeutic effect on the adjuvant-induced arthritis in rats. Therefore, the class of tetrahydronaphtho [1,2-b]furan-2(3H)-one derivatives provided herein are applicable to the preparation of a drug for treating rheumatoid arthritis.

What is claimed is:

1. A tetrahydronaphtho[1,2-b]furan-2(3H)-one derivative of formula (I):

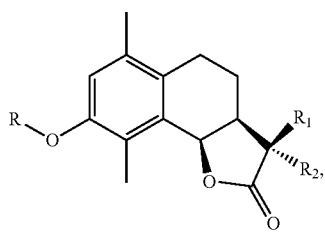

(I)

wherein:

R is selected from the group consisting of hydrogen, alkyl, cycloalkyl, hydroxy-substituted alkyl, alkenyl, alkynyl, aryl, alkylaryl, arylalkyl, arylalkenyl, arylalkynyl, heterocyclic group, trifluoromethyl, polyfluorosubstituted alkyl, cyano, cyanomethyl, acyl, carbamoyl, sulfonyl, sulfonamido and aryloxyalkyl;

$R_1$ is hydrogen or deuterium and $R_2$ is

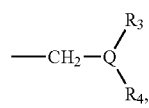

or a pharmaceutically acceptable salt thereof formed by a reaction with an acid L or a quaternary ammonium salt thereof formed by a reaction with $R_5Z$, wherein Z is selected from the group consisting of fluorine, chlorine, bromine, iodine, p-toluenesulfonate, methanesulfonate, benzenesulfonate and trifluoromethanesulfonate; $R_5$ is selected from the group consisting of hydrocarbyl, cycloalkyl, hydroxy-substituted alkyl, alkenyl, alkynyl, aryl, heterocyclic group, aryl-substituted alkyl, arylalkenyl, arylalkynyl, cyano-substituted methyl, alkoxy-substituted alkyl and aryloxy-substituted alkyl; Q is N, O or S;

wherein the acid L is an inorganic acid or an organic acid; wherein the inorganic acid is selected from the group consisting of hydrofluoric acid, hydrochloric acid, hydrobromic acid, hydroiodic acid, sulfuric acid, sulfurous acid, nitric acid, phosphoric acid, phosphorous acid, carbonic acid, boric acid, selenious acid and phosphomolybdic acid; the organic acid is selected from the group consisting of acetic acid, propionic acid, hexanoic acid, oxalic acid, trifluoroacetic acid, glycolic acid, lactic acid, pyruvic acid, malonic acid, succinic acid, maleic acid, fumaric acid, hydroxymaleic acid, malic acid, tartaric acid, citric acid, mandelic acid, cinnamic acid, amino acid, benzoic acid, salicylic acid, 4-aminosalicylic acid, isonicotinic acid, methanesulfonic acid, ethanesulfonic acid, 2-hydroxyethanesulfonic acid, 1,2-ethanedisulfonic acid, benzenesulfonic acid, p-toluenesulfonic acid, naphthalene-2-sulfonic acid and camphorsulfonic acid, wherein the amino acid is selected from glycine, glutamic acid, proline, arginine and lysine;

$R_3$ and $R_4$ are independently selected from the group consisting of hydrogen, alkyl, cycloalkyl, hydroxy-substituted alkyl, alkenyl, alkynyl, aryl, alkylaryl, arylalkyl, arylalkenyl, arylalkynyl, heterocyclic group, trifluoromethyl, polyfluorosubstituted alkyl, cyano, cyanomethyl, acyl, carbamoyl, sulfonyl, sulfonamido and aryloxyalkyl; wherein $R_3$ and $R_4$ are the same or different.

2. The tetrahydronaphtho[1,2-b]furan-2(3H)-one derivative of claim 1, wherein $R_3$ and $R_4$ form a 3- to 9-membered cyclic structure with a nitrogen atom, wherein the cyclic structure further comprises one or more substituents selected from the group consisting of hydrogen, alkyl, cycloalkyl, alkenyl, alkynyl, aryl, alkylaryl, arylalkyl, arylalkenyl, arylalkynyl and heterocyclic group.

3. The tetrahydronaphtho[1,2-b]furan-2(3H)-one derivative of claim 1, wherein the tetrahydronaphtho[1,2-b]furan-2(3H)-one derivative is selected from the group consisting of following compounds:

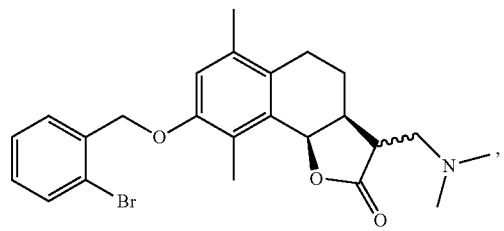

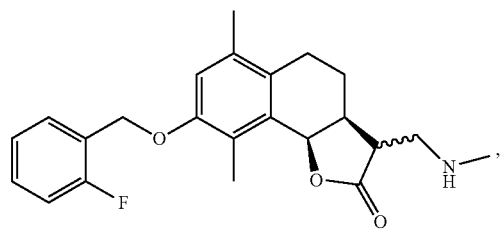

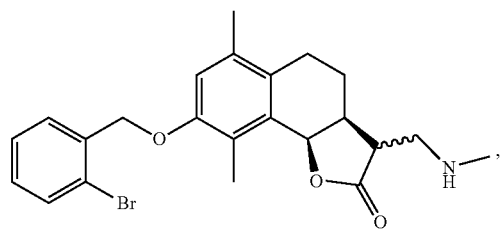

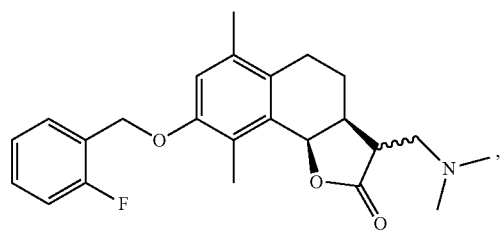

-continued

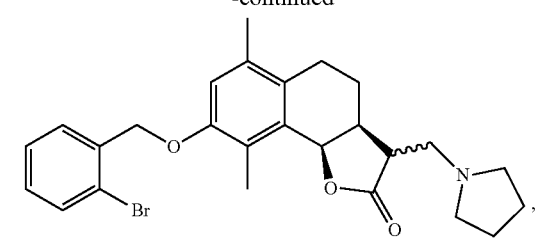

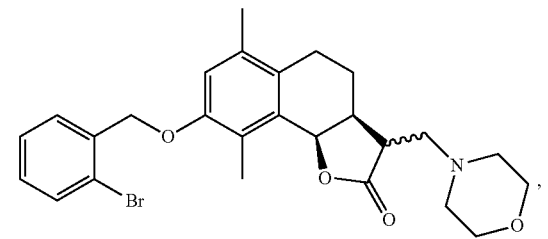

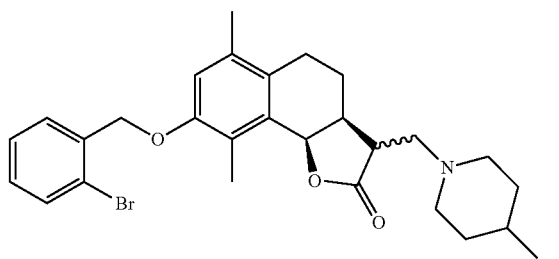

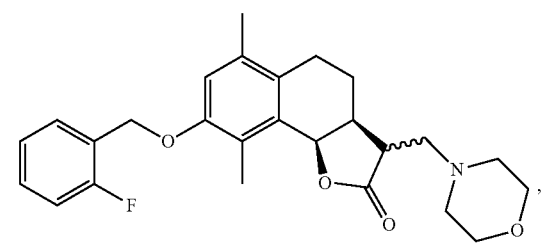

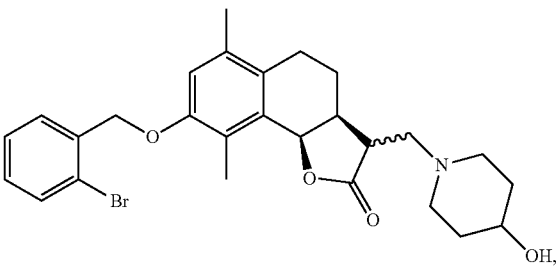

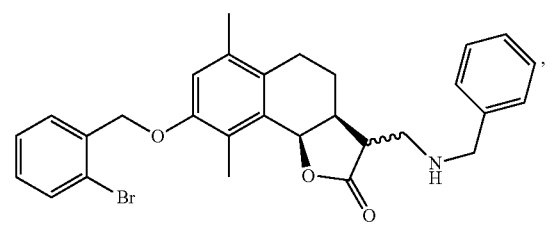

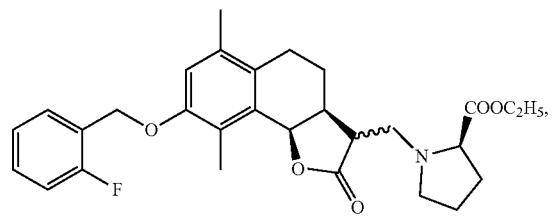

-continued

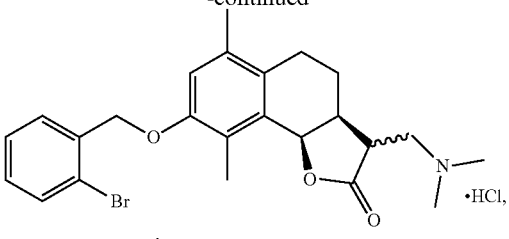

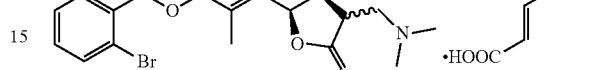

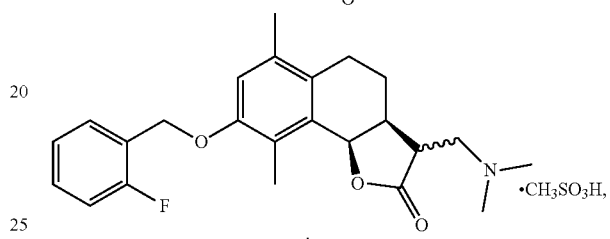

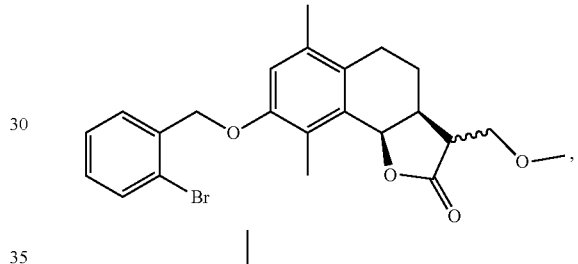

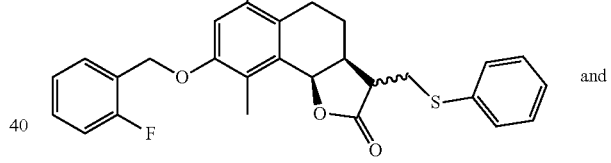

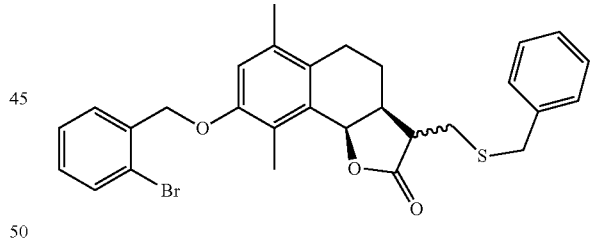

and

4. A method of preparing the tetrahydronaphtho[1,2-b]furan-2(3H)-one derivative of claim 1, comprising:
(1) subjecting (3aS,5aS,9bS)-5a,9-dimethyl-3-methylene-3a,5,5a, 9b-tetrahydronaphtho[1,2-b]furan-2,8(3H,4H)-dione (compound II) to rearrangement reaction in a solvent under an acidic condition in the presence of a catalyst to form (3aS,9bR)-6,9-dimethyl-3-methylene-2-oxo-2,3,3a,4,5,9b-hexahydronaphtho[1,2-b]furan-8-yl acetate (compound 1);
(2) hydrolyzing a phenolic ester bond of the compound 1 in a solvent under a basic condition in the presence of a catalyst to produce (3aS,9bR)-8-hydroxy-6,9-dimethyl-3-methylene-3a,4,5,9 b-tetrahydronaphtho[1,2-b]furan-2(3H)-one (compound 2);
(3) subjecting a free phenolic hydroxyl group of the compound 2 and a halogenated alkane to nucleophilic substitution in a solvent in the presence of a base and a catalyst to produce (3aS,9bR)-8-alkoxy-6,9-dimethyl-3-methylene-3a,4,5,9b-tetrahydronaphtho[1,2-b]furan-2(3H)-one (compound III), wherein the halogenated alkane is a halobenzyl or haloalkyl;

(4) subjecting an α-methylene lactone ring of the compound III and a nucleophile to Michael addition in a solvent in the presence of a base to form (3R or 3S,3aS,9bR)-8-substituted alkoxy-3-(substituted) aminomethyl/alkoxy/alkylthio-6,9-dimethyl-3a,4,5,9b-tetrahydronaphtho[1,2-b]furan-2(3H)-one (compound IV), wherein the nucleophile is an oxygen-containing alcohol or phenol, a nitrogen-containing aliphatic or aromatic amine or a sulfur-containing thiophenol or thiol; and (5) subjecting the compound IV and the acid L to salt-formation reaction in a solvent to produce a pharmaceutically-acceptable salt (compound V) of (3R or 3S,3aS,9bR)-8-substituted alkoxy-3-disubstituted amino methyl-6,9-dimethyl-3a,4,5,9b-tetrahydronaphtho[1,2-b]furan-2(3H)-one, as shown in the following scheme:

8. The method of claim 7, wherein the rearrangement reaction is performed at 0° C.-5° C.; and the molar ratio of the catalyst to the compound II is 1:3-1:1.

9. The method of claim 4, wherein in step (2), the solvent is selected from the group consisting of methanol, ethanol, isopropanol, toluene, tetrahydrofuran, 2-methyltetrahydrofuran, dioxane, dichloromethane, dichloroethane, acetone and butanone; the catalyst is selected from the group consisting of ammonia water, diethylamine, ethanolamine, formic acid and trifluoroacetic acid; the hydrolysis is performed at −20° C.-25° C.; and a molar ratio of the catalyst to the compound 1 is 30:1-1:1.

10. The method of claim 9, wherein the solvent is methanol or tetrahydrofuran; the hydrolysis is performed at −5° C.-15° C.; and the molar ratio of the catalyst to the compound 1 is 20:1-1:1.

11. The method of claim 10, wherein the hydrolysis is performed at 0° C.-5° C.; and the molar ratio of the catalyst to the compound 1 is 5:1-1:1.

12. The method of claim 4, wherein in step (3), the solvent is selected from methanol, ethanol, isopropanol, dimethyl sulfoxide, N,N-dimethylformamide, toluene, xylene, tetra-

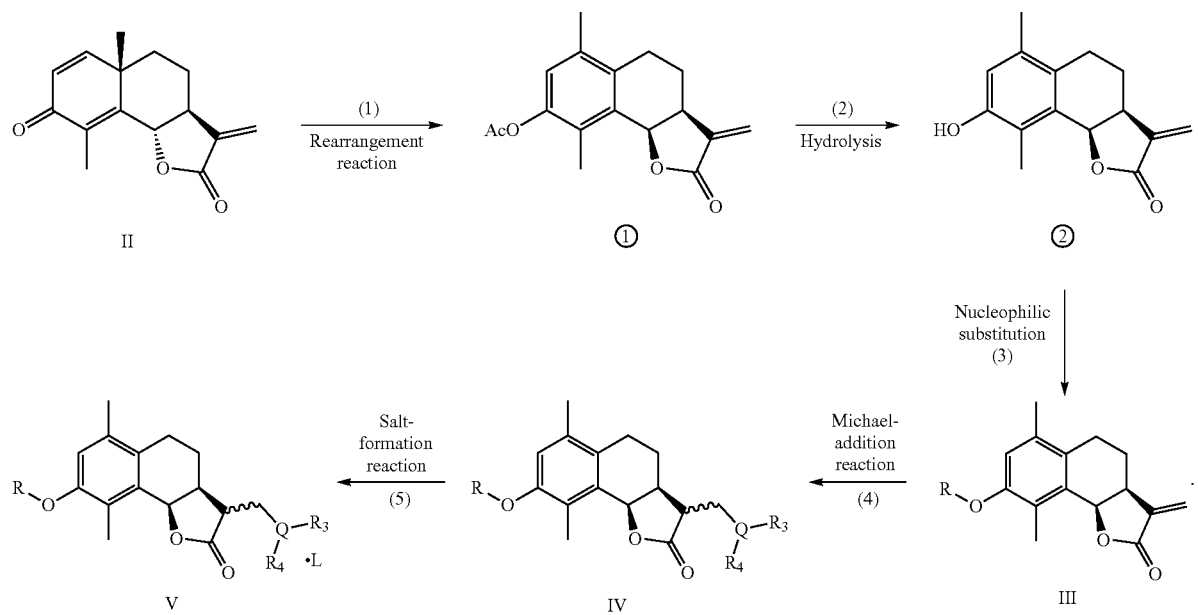

5. The method of claim 4, wherein R3 and R4 form a 3- to 9-membered cyclic structure with a nitrogen atom, wherein the cyclic structure further comprises one or more substituents selected from the group consisting of hydrogen, alkyl, cycloalkyl, alkenyl, alkynyl, aryl, alkylaryl, arylalkyl, arylalkenyl, arylalkynyl and heterocyclic group.

6. The method of claim 4, wherein in step (1), the solvent is selected from the group consisting of toluene, xylene, tetrahydrofuran, 2-methyltetrahydrofuran, dioxane, dichloromethane and dichloroethane; the catalyst is acetic anhydride or acetic acid/sulfuric acid; the rearrangement reaction is performed at −20° C.-25° C.; and a molar ratio of the catalyst to the compound II is 1:20-1:1.

7. The method of claim 6, wherein the solvent is toluene or tetrahydrofuran; the rearrangement reaction is performed at −5° C.-15° C.; and the molar ratio of the catalyst to the compound 2 is 1:10-1:1.

hydrofuran, 2-methyltetrahydrofuran, ethyl acetate, dichloromethane, dichloroethane, chloroform, acetone and butanon; the base is an organic or inorganic base, wherein the organic base is selected from the group consisting of diethylamine, triethylamine, pyridine, piperidine, 4-dimethylaminopyridine, N,N-diisopropylethylamine, 1,8-diazabicycloundec-7-ene and 1,4-diazabicyclo[2.2.2]octane; the inorganic base is selected from the group consisting of sodium hydroxide, potassium hydroxide, potassium carbonate, sodium carbonate, cesium carbonate, potassium bicarbonate, sodium bicarbonate, sodium acetate, potassium acetate, sodium phosphate and potassium phosphate; the catalyst is selected from the group consisting of tetrabutylammonium chloride, tetrabutylammonium bromide, tetrabutylammonium iodide, tetrabutylammonium hydrogen sulfate, benzyltriethylammonium chloride and dodecyltriethylammonium chloride; the nucleophilic substitution is performed at −30° C.-60° C.; a molar ratio of the base to the compound 2 is 6:1-1:1; and a molar ratio of the catalyst to the compound 2 is 1:20-1:1.

13. The method of claim 12, wherein the solvent is acetone, ethanol or tetrahydrofuran; the base is triethylamine, sodium acetate or potassium acetate; the catalyst is tetrabutylammonium iodide; the nucleophilic substitution is performed at −10° C.-35° C.; the molar ratio of the base to the compound 2 is 3:1-1:1; and the molar ratio of the catalyst to the compound 2 is 1:10-1:1.

14. The method of claim 13, wherein the nucleophilic substitution is performed at 0° C.-25° C.; the molar ratio of the base to the compound 2 is 2:1-1:1; and the molar ratio of the catalyst to the compound 2 is 1:3-1:1.

15. The method of claim 4, wherein in step (4), the solvent is selected from methanol, ethanol, propanol, isopropanol, dimethyl sulfoxide, N,N-dimethylformamide, toluene, xylene, tetrahydrofuran, 2-methyltetrahydrofuran, ethyl acetate, dichloromethane, dichloroethane, chloroform, acetone and butanone; the base is an organic or inorganic base, wherein the organic base is selected from the group consisting of diethylamine, triethylamine, pyridine, piperidine, 4-dimethylaminopyridine, N,N-diisopropylethylamine, 1,8-diazabicycloundec-7-ene and 1,4-diazabicyclo[2.2.2]octane; the inorganic base is selected from the group consisting of sodium hydroxide, potassium hydroxide, potassium carbonate, sodium carbonate, cesium carbonate, potassium bicarbonate, sodium bicarbonate, sodium acetate, potassium acetate, sodium phosphate and potassium phosphate; the Michael addition is performed at −30° C.-60° C.; and a molar ratio of the base to the compound III is 8:1-1:1.

16. The method of claim 15, wherein the solvent is methanol, ethanol or tetrahydrofuran; the base is triethylamine, sodium acetate or potassium acetate; the Michael addition is performed at −10° C.-35° C.; the molar ratio of the base to the compound III is 5:1-1:1.

17. The method of claim 4, wherein in step (5), the solvent is selected from methanol, ethanol, isopropanol, dimethyl sulfoxide, N,N-dimethylformamide, toluene, xylene, tetrahydrofuran, 2-methyltetrahydrofuran, ethyl acetate, dichloromethane, dichloroethane, chloroform, acetone and butanone; the salt-formation reaction is performed at 0° C.-60° C.; the acid is an inorganic acid or an organic acid, wherein the inorganic acid is selected from the group consisting of hydrochloric acid, hydrobromic acid, sulfuric acid, nitric acid and phosphoric acid; the organic acid is selected from the group consisting of acetic acid, propionic acid, hexanoic acid, oxalic acid, trifluoroacetic acid, glycolic acid, pyruvic acid, malonic acid, succinic acid, maleic acid, fumaric acid, hydroxymaleic acid, malic acid, tartaric acid, citric acid, mandelic acid, cinnamic acid, amino acid, benzoic acid, salicylic acid, 4-aminosalicylic acid, isonicotinic acid, methanesulfonic acid, ethanesulfonic acid, 2-hydroxyethanesulfonic acid, 1,2-ethanedisulfonic acid, benzenesulfonic acid, p-toluenesulfonic acid, naphthalene-2-sulfonic acid and camphorsulfonic acid, wherein the amino acid is selected from glycine, glutamic acid, arginine and lysine; and a molar ratio of the acid L to the compound IV is 3:1-1:8.

18. The method of claim 17, wherein the solvent is ethanol or dichloromethane; the salt-formation reaction is performed at 5° C.-35° C.; and the molar ratio of the acid L to the compound IV is 1:1-1:5.

19. A method of treating rheumatoid arthritis in a patient in need thereof, comprising:
    administering an effective amount of a pharmaceutical composition comprising the tetrahydronaphtho[1,2-b]furan-2(3H)-one derivative of claim 1 as an active ingredient to the patient.

20. The method of claim 19, wherein the pharmaceutical composition further comprises a pharmaceutically-acceptable adjuvant, and a dosage form of the pharmaceutical composition is tablet, dispersible tablet, buccal tablet, orally disintegrating tablet, sustained release tablet, capsule, soft capsule, dripping pill, granule, injection, powder injection, or aerosol.

\* \* \* \* \*